United States Patent
Tsumaki et al.

(10) Patent No.: US 10,073,083 B2
(45) Date of Patent: Sep. 11, 2018

(54) PROPHYLACTIC AND THERAPEUTIC AGENTS FOR FGFR3 DISEASES AND SCREENING METHOD FOR THE SAME

(71) Applicant: KYOTO UNIVERSITY, Kyoto (JP)

(72) Inventors: Noriyuki Tsumaki, Kyoto (JP); Akihiro Yamashita, Kyoto (JP)

(73) Assignee: Kyoto University, Kyoto (JP)

(*) Notice: Subject to any disclaimer, the term of this patent is extended or adjusted under 35 U.S.C. 154(b) by 0 days.

(21) Appl. No.: 15/100,732

(22) PCT Filed: Nov. 25, 2014

(86) PCT No.: PCT/JP2014/081093
§ 371 (c)(1),
(2) Date: Jul. 27, 2016

(87) PCT Pub. No.: WO2015/083582
PCT Pub. Date: Jun. 11, 2015

(65) Prior Publication Data
US 2016/0327544 A1 Nov. 10, 2016

(30) Foreign Application Priority Data

Dec. 2, 2013 (JP) ................. 2013-249221
Aug. 26, 2014 (JP) ................. 2014-171078

(51) Int. Cl.
| | |
|---|---|
| *A61K 31/22* | (2006.01) |
| *G01N 33/50* | (2006.01) |
| *A61K 31/366* | (2006.01) |
| *A61K 31/40* | (2006.01) |
| *A61K 31/404* | (2006.01) |
| *A61K 31/505* | (2006.01) |
| *C12N 5/077* | (2010.01) |
| *C12N 5/074* | (2010.01) |
| *C12Q 1/6883* | (2018.01) |

(52) U.S. Cl.
CPC ......... *G01N 33/5044* (2013.01); *A61K 31/22* (2013.01); *A61K 31/366* (2013.01); *A61K 31/40* (2013.01); *A61K 31/404* (2013.01); *A61K 31/505* (2013.01); *C12N 5/0655* (2013.01); *C12N 5/0696* (2013.01); *C12Q 1/6883* (2013.01); *G01N 33/5073* (2013.01); *C12N 2501/115* (2013.01); *C12N 2501/119* (2013.01); *C12N 2501/15* (2013.01); *C12N 2501/155* (2013.01); *C12N 2501/19* (2013.01); *C12N 2506/45* (2013.01); *C12N 2510/00* (2013.01); *C12Q 2600/136* (2013.01); *C12Q 2600/158* (2013.01)

(58) Field of Classification Search
CPC ........... G01N 33/5044; G01N 33/5073; C12N 5/0655; C12N 5/0696; C12N 2501/115; C12N 2501/19; A61K 31/22; A61K 31/40; A61K 31/404; A61K 31/505; A61K 31/366; C12Q 1/6883; C12Q 2600/158; C12Q 2600/136
See application file for complete search history.

(56) References Cited

U.S. PATENT DOCUMENTS

| | | |
|---|---|---|
| 2004/0014024 A1 | 1/2004 | Yayon et al. |
| 2004/0109850 A1 | 6/2004 | Jaiswal et al. |
| 2009/0047263 A1 | 2/2009 | Yamanaka et al. |
| 2009/0068742 A1 | 3/2009 | Yamanaka |
| 2009/0181098 A1 | 7/2009 | Garrett et al. |
| 2009/0227032 A1 | 9/2009 | Yamanaka et al. |
| 2009/0247576 A1 | 10/2009 | Kamata |
| 2010/0062533 A1 | 3/2010 | Yamanaka |
| 2010/0210014 A1 | 8/2010 | Yamanaka |
| 2010/0216236 A1 | 8/2010 | Yamanaka |
| 2013/0059386 A1 | 3/2013 | Yamanaka et al. |

FOREIGN PATENT DOCUMENTS

| | | |
|---|---|---|
| JP | 2009-529051 | 8/2009 |
| WO | 00/46343 | 8/2000 |
| WO | 02/50246 | 6/2002 |
| WO | 2007/061130 | 5/2007 |
| WO | 2007/069666 | 6/2007 |

OTHER PUBLICATIONS

International Search Report dated Mar. 3, 2015 in International Application No. PCT/JP2014/081093.
International Preliminary Report on Patentability dated Jun. 7, 2016 in International Application No. PCT/JP2014/081093.
Simopoulou, T. et al., Protective Effect of Atorvastatin in Cultured Osteoarthritic Chondrocytes, Journal of Orthopaedic Research, 2010, vol. 28, p. 110-115.
Kramer, J. et al., Simvastatin modulates mouse embryonic stem cell-derived chondrogenesis in vitro, Toxicology In Vitro, 2012, vol. 26, No. 7, p. 1170-1176.
Legeai-Mallet, L. et al., Overexpression of FGFR3, Stst1, Stat5, and p21Cip1 correlates with phenotypic severity and defective chondrocyte differentiation in FGFR3-related chondrodysplasias, Bone, 2004, vol. 34, p. 26-36.
Chen, L. et al., Gly369Cys mutation in mouse FGFR3 causes achondroplasia by affecting both chondrogenesis and osteogenesis, The Journal of Clinical Investigation, 1999, vol. 104, No. 11, p. 1517-1525.

(Continued)

*Primary Examiner* — Sudhakar Katakam
(74) *Attorney, Agent, or Firm* — Wenderoth, Lind & Ponack, L.L.P.

(57) ABSTRACT

The present invention provides a therapeutic and/or prophylactic medicament for FGFR3 diseases, the medicament comprising a HMG-CoA reductase inhibitor as an active ingredient; a method for treating and/or preventing FGFR3 diseases, the method comprising administering a HMG-CoA reductase inhibitor; use of a HMG-CoA reductase inhibitor in the production of a therapeutic and/or prophylactic medicament for FGFR3 diseases; and a method for screening for a therapeutic and/or prophylactic drug for FGFR3 diseases.

4 Claims, 22 Drawing Sheets

Specification includes a Sequence Listing.

(56) References Cited

OTHER PUBLICATIONS

Shohei Kasugai, "Kotsutaisha Shikkan no Seiin to Chiryo-Kiso to Rinsho o Tsunagu Mono-Statin no Kyokusho Tekiyo ni yoru Kotsuzosei", Clin Calcium, 2005, vol. 15, No. 7, 1165-70.
Jadhav, S.B. et al, Statins and osteoporosis: new role for old drugs, J Pharm Pharmacol, 2006, vol. 58, No. 1, p. 3-18.
Yamashita, A. et al., Statin treatment rescues FGFR3 skeletal dysplasia phenotypes, Nature, 2014, vol. 513, No. 7519, p. 507-511.
Jonquoy, A., et al., Hum Mol Genet 21 : 841-851 (2012).
Rauchenberger, R., et al., J Biol Chem 278 : 38194-38205 (2003).
Yasoda, A., et al., Endocrinology 150 : 3138-3144 (2009).
Takahashi, K, et al., Cell. 131 : 861-872 (2007).
Extended European Search Report dated Oct. 16, 2017 in European Application No. 14867427.8.

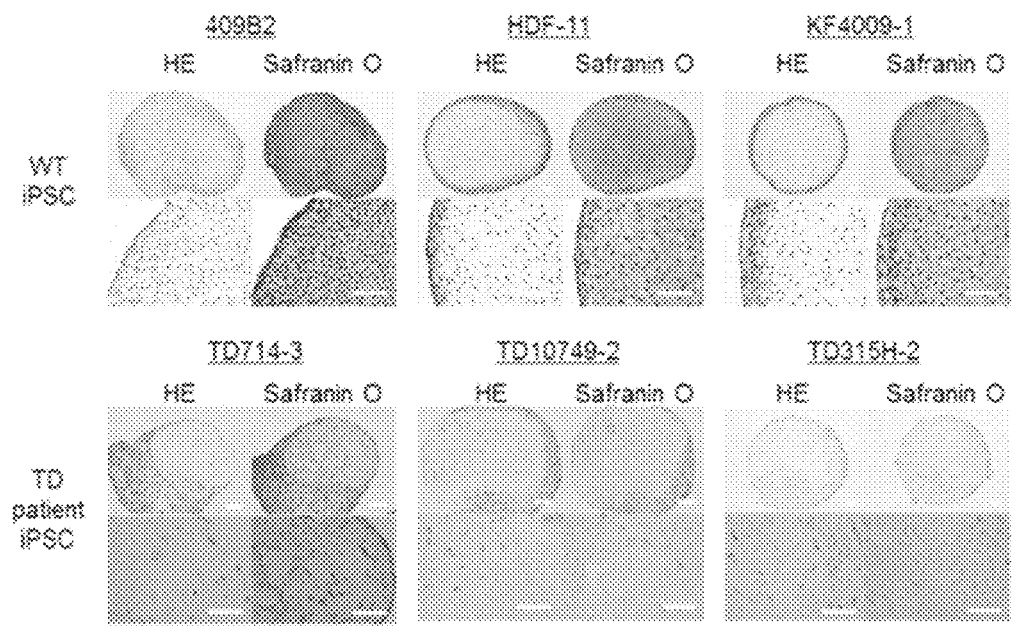

Fig. 7A
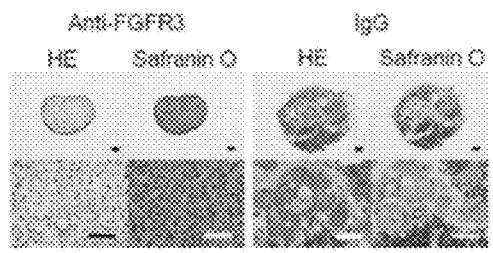
Fig. 7B
| antibody | Anti-FGFR3 | IgG |
|---|---|---|
| Safranin O positive / total particles | 2 / 3 | 0 / 3 |
Fig. 7C
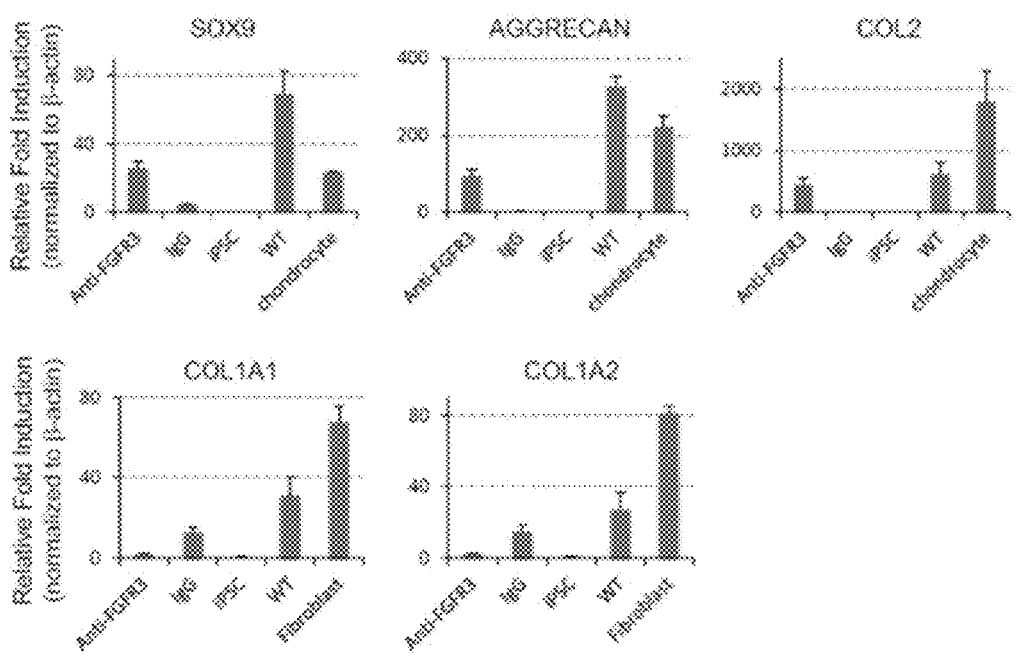

Fig. 8A
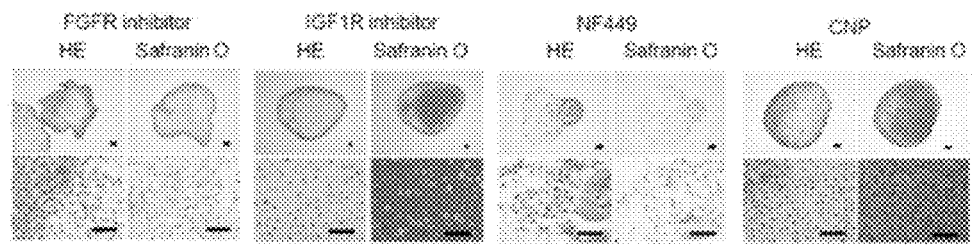
Fig. 8B
| compound | FGFR inhibitor | IGF1R inhibitor | CNP | NF449 | Vehicle |
|---|---|---|---|---|---|
| Safranin O positive / total particles | 0 / 10 | 2 / 10 | 7 / 10 | 0 / 10 | 0 / 10 |
Fig. 8C
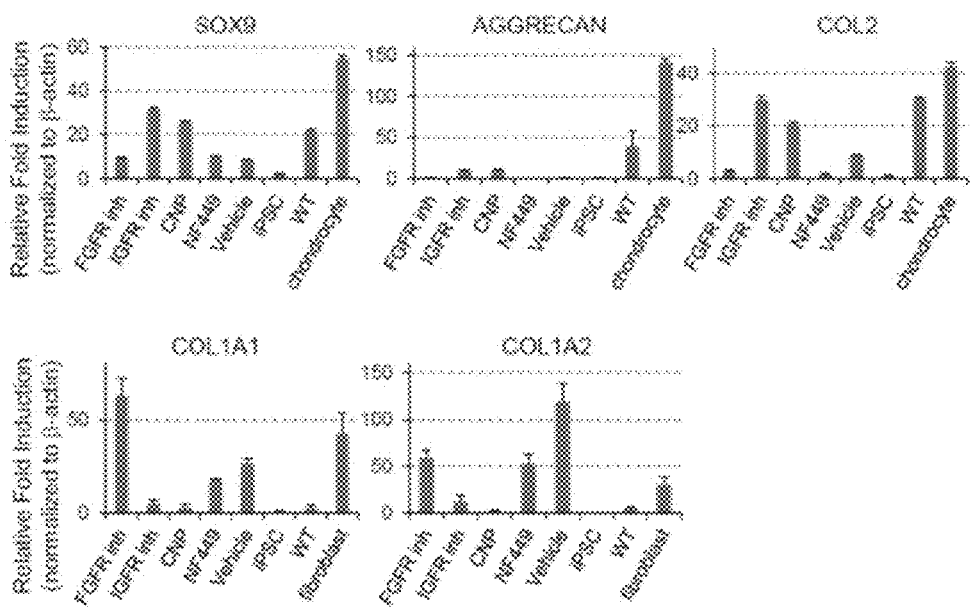

Fig. 9A
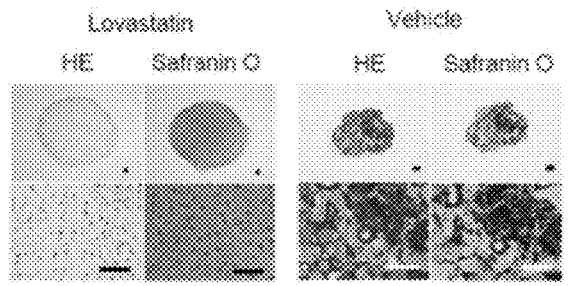
Fig. 9B
| Compounds | Lovastatin | Vehicle |
|---|---|---|
| Safranin O positive / total particles | 8 / 10 | 0 / 10 |
Fig. 9C
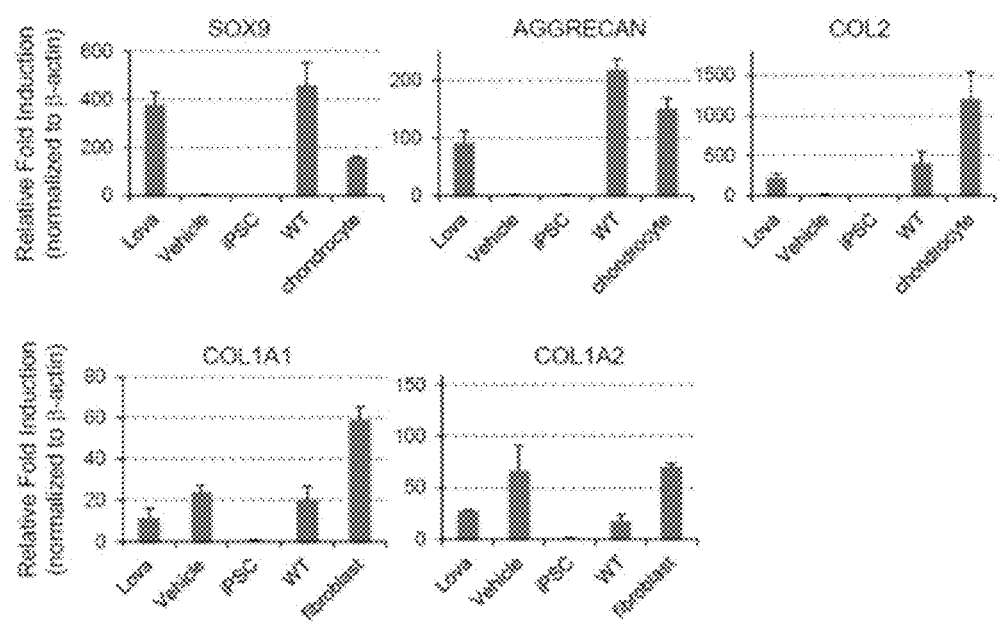

SEQUENCE LISTING

```
<160> NUMBER OF SEQ ID NOS: 20

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1
tggcaccaca ccttctacaa tgagc                                          25

<210> SEQ ID NO 2
<211> LENGTH: 25
<212> TYPE: DNA
<213> ORGANISM: Artificial sequence
<220> FEATURE:
<223> OTHER INFORMATION: Primer

<400> SEQUENCE: 2
gcacagcttc tccttaatgt cacgc                                          25

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3
agacctttgg gctgccttat                                                20

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tagcctccct cactccaaga                                                20

<210> SEQ ID NO 5
<211> LENGTH: 23
<212> TYPE: DNA
<213> ORGANISM: Artificial sequence
<220> FEATURE:
```

<223> OTHER INFORMATION: Primer

<400> SEQUENCE: 5
tgaggagggc tggaacaagt acc                                    23

<210> SEQ ID NO 6
<211> LENGTH: 23
<212> TYPE: DNA
<213> ORGANISM: Artificial sequence
<220> FEATURE:
<223> OTHER INFORMATION: Primer

<400> SEQUENCE: 6
ggaggtggta attgcaggga aca                                    23

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
tttcccaggt caagatggtc                                        20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
cttcagcacc tgtctcacca                                        20

<210> SEQ ID NO 9
<211> LENGTH: 19
<212> TYPE: DNA
<213> ORGANISM: Artificial sequence
<220> FEATURE:
<223> OTHER INFORMATION: Primer

<400> SEQUENCE: 9
gtcgagggcc aagacgaag                                         19

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
cagatcacgt catcgcacaa c                                      21

<210> SEQ ID NO 11
<211> LENGTH: 21
<212> TYPE: DNA
<213> ORGANISM: Artificial sequence
<220> FEATURE:
<223> OTHER INFORMATION: Primer

<400> SEQUENCE: 11
aattggagct gttggtaacg c                                      21

```
<210> SEQ ID NO 12
<211> LENGTH: 19
<212> TYPE: DNA
<213> ORGANISM: Artificial sequence
<220> FEATURE:
<223> OTHER INFORMATION: Primer

<400> SEQUENCE: 12
caccagtaag gccgtttgc                                                   19

<210> SEQ ID NO 13
<211> LENGTH: 77
<212> TYPE: DNA
<213> ORGANISM: Artificial sequence
<220> FEATURE:
<223> OTHER INFORMATION: Primer

<400> SEQUENCE: 13
gatcctacac ctgcgtcgtg gagaacaagt ttgtgaagca gatgaaactt gttctccacg       60
acgcaggtgt atttttg                                                     77

<210> SEQ ID NO 14
<211> LENGTH: 77
<212> TYPE: DNA
<213> ORGANISM: Artificial sequence
<220> FEATURE:
<223> OTHER INFORMATION: Primer

<400> SEQUENCE: 14
aattcaaaaa tacacctgcg tcgtggagaa caagtttcat ctgcttcaca aacttgttct       60
ccacgacgca ggtgtag                                                     77

<210> SEQ ID NO 15
<211> LENGTH: 77
<212> TYPE: DNA
<213> ORGANISM: Artificial sequence
<220> FEATURE:
<223> OTHER INFORMATION: Primer

<400> SEQUENCE: 15
gatccgatgc tgaaagacga tgccactgac aacatctgct tcacttgtca gtggcatcgt       60
ctttcagcat cttttg                                                      77

<210> SEQ ID NO 16
<211> LENGTH: 77
<212> TYPE: DNA
<213> ORGANISM: Artificial sequence
<220> FEATURE:
<223> OTHER INFORMATION: Primer

<400> SEQUENCE: 16
aattcaaaaa gatgctgaaa gacgatgcca ctgacaagtg aagcagatgt tgtcagtggc       60
atcgtctttc agcatcg                                                     77

<210> SEQ ID NO 17
<211> LENGTH: 77
<212> TYPE: DNA
<213> ORGANISM: Artificial sequence
<220> FEATURE:
<223> OTHER INFORMATION: Primer

<400> SEQUENCE: 17
gatccctgca cacgacct gtacatgatc atcatctgct tcacatgatc atgtacaggt        60
```

```
cgtgtgtgca gttttttg                                                    77

<210> SEQ ID NO 18
<211> LENGTH: 77
<212> TYPE: DNA
<213> ORGANISM: Artificial sequence
<220> FEATURE:
<223> OTHER INFORMATION: Primer

<400> SEQUENCE: 18
aattcaaaaa ctgcacacac gacctgtaca tgatcatgtg aagcagatga tgatcatgta    60
caggtcgtgt gtgcagg                                                    77

<210> SEQ ID NO 19
<211> LENGTH: 75
<212> TYPE: DNA
<213> ORGANISM: Artificial sequence
<220> FEATURE:
<223> OTHER INFORMATION: Primer

<400> SEQUENCE: 19
gatccgtgcg ttgttagtac taatcctatt tgtgaagcag atgaaatagg gttggtacta    60
gcaacgcact ttttg                                                      75

<210> SEQ ID NO 20
<211> LENGTH: 75
<212> TYPE: DNA
<213> ORGANISM: Artificial sequence
<220> FEATURE:
<223> OTHER INFORMATION: Primer

<400> SEQUENCE: 20
aattcaaaaa gtgcgttgct agtaccaacc ctatttcatc tgcttcacaa ataggattag    60
tactaacaac gcacg                                                      75
```

PROPHYLACTIC AND THERAPEUTIC AGENTS FOR FGFR3 DISEASES AND SCREENING METHOD FOR THE SAME

TECHNICAL FIELD

The present invention relates to a screening method for a therapeutic and/or prophylactic agent for fibroblast growth factor receptor 3 (FGFR3) diseases. The present invention also relates to a therapeutic agent for FGFR3 diseases.

BACKGROUND ART

Skeletal diseases associated with abnormal bone formation, as exemplified by thanatophoric dysplasia (TD) and achondroplasia (ACH), are commonly called fibroblast growth factor receptor 3 (FGFR3) diseases. FGFR3 diseases are considered to be caused by gain-of-function mutations in FGFR3. FGFR3 and various molecules in the downstream signaling pathways of FGFR3 have gained attention as molecular targets for treating the diseases, and various approaches to inhibition of excessive signaling from FGFR3 have been attempted.

Several techniques for inhibiting excessive signaling from FGFR3 have previously been described, including the tyrosine kinase inhibitor reported by Jonquoy et al. (Non Patent Literature 1), the FGFR3 neutralizing antibodies reported by Rauchenberger et al. (Non Patent Literature 2), and c-type natriuretic peptide (CNP) reported by Yasoda et al. (Non Patent Literature 3). Some of these approaches successfully restored bone growth in model mice of FGFR3-related chondrodysplasia. However, the restoring effect was only confirmed in transformed cells transduced with mutant FGFR3, and the efficacy has yet to be investigated in appropriate human cell models. Also, it remains largely uncertain whether such approaches have sufficient therapeutic potential for FGFR3 diseases. These circumstances have raised demand for the development of a novel therapeutic drug.

In the field of regenerative medicine, there has been demand for techniques for converting versatile cells usable as a biomaterial into the desired cell type. Recently established are mouse or human-derived induced pluripotent stem (iPS) cells. Yamanaka et al. succeeded in establishing iPS cells by introducing the four genes, Oct3/4, Sox2, Klf4 and c-Myc, into human dermal fibroblasts (Patent Literature 1 and Non Patent Literature 4). By this technique, iPS cells can be generated from the cells of a patient to be treated and then differentiated into various types of tissue cells, and thereby can be used to reproduce the patient's clinical conditions in vitro. However, in terms of FGFR3 diseases, successful generation of iPS cells from the somatic cells of a FGFR3 disease patient has not been reported.

CITATION LIST

Patent Literature

Patent Literature 1: WO 2007/069666

Non Patent Literature

Non Patent Literature 1: Jonquoy, A., et al., Hum Mol Genet 21: 841-851 (2012).
Non Patent Literature 2: Rauchenberger, R., et al., J Biol Chem 278: 38194-38205 (2003).
Non Patent Literature 3: Yasoda, A., et al., Endocrinology 150: 3138-3144 (2009).
Non Patent Literature 4: Takahashi, K, et al., Cell. 131: 861-872 (2007).

SUMMARY OF INVENTION

Technical Problem

An object of the present invention is to provide a screening method for a therapeutic and/or prophylactic agent for fibroblast growth factor receptor 3 (FGFR3) diseases. Another object of the present invention is to provide a therapeutic agent for FGFR3 diseases.

Solution to Problem

The inventors conducted extensive studies to solve the above problems and successfully reproduced the clinical conditions of FGFR3 diseases by inducing chondrogenic differentiation of iPS cells derived from the somatic cells of FGFR3 disease patients. That is, the inventors found that iPS cells derived from the somatic cells of FGFR3 disease patients tend to poorly differentiated into chondrocytes as compared with iPS cells derived from normal individuals. The inventors performed screening for therapeutic and/or prophylactic agents for FGFR3 diseases using the iPS cells derived from the somatic cells of FGFR3 disease patients, and as a result, found that drugs used for treatment of hyperlipemia promote the differentiation of the iPS cells toward chondrocytes. Based on these findings, the inventors completed the present invention.

That is, the present invention provides the following.
[1] A therapeutic and/or prophylactic medicament for a FGFR3 disease, the medicament comprising a HMG-CoA reductase inhibitor as an active ingredient.
[2] The medicament of the above [1], wherein the HMG-CoA reductase inhibitor is a drug selected from the group consisting of mevastatin, atorvastatin, pravastatin, rosuvastatin, fluvastatin and lovastatin.
[3] The medicament of the above [1] or [2], wherein the FGFR3 disease is thanatophoric dysplasia (TD) and/or achondroplasia (ACH).
[4] A method for treating and/or preventing a FGFR3 disease, the method comprising administering a HMG-CoA reductase inhibitor.
[5] The method of the above [4], wherein the HMG-CoA reductase inhibitor is a drug selected from the group consisting of mevastatin, atorvastatin, pravastatin, rosuvastatin, fluvastatin and lovastatin.
[6] The method of the above [4] or [5], wherein the FGFR3 disease is thanatophoric dysplasia (TD) and/or achondroplasia (ACH).
[7] Use of a HMG-CoA reductase inhibitor in the production of a therapeutic and/or prophylactic medicament for a FGFR3 disease.
[8] The use of the above [7], wherein the HMG-CoA reductase inhibitor is a drug selected from the group consisting of mevastatin, atorvastatin, pravastatin, rosuvastatin, fluvastatin and lovastatin.
[9] The use of the above [7] or [8], wherein the FGFR3 disease is thanatophoric dysplasia (TD) and/or achondroplasia (ACH).
[10] A method for screening for a therapeutic and/or prophylactic drug for a FGFR3 disease, the method comprising the steps of:

(a) differentiating induced pluripotent stem (iPS) cells having a FGFR3 mutation into chondrocytes under conditions where the cells are in contact with a test substance and under conditions where the cells are not in contact with the test substance,
(b) measuring one or more indicators selected from the group consisting of the amount of cartilaginous extracellular matrix, the expression level of a chondrocyte marker gene, and the expression level of a fibroblast marker gene in cultures resulting from step (a), and
(c) identifying the test substance as a therapeutic or prophylactic drug for a FGFR3 disease when the chondrocytes differentiated in contact with the test substance show an increased amount of the cartilaginous extracellular matrix, an increased expression level of the chondrocyte marker gene, or a decreased expression level of the fibroblast marker gene, as compared with the chondrocytes differentiated not in contact with the test substance.

[11] The method of the above [10], wherein step (a) for differentiation into chondrocytes comprises the steps of:
(i) inducing mesodermal cells from pluripotent stem cells in adherent culture,
(ii) culturing the cells obtained by step (i) in adherent culture in a medium containing bFGF, ascorbic acid, BMP2, TGFβ, GDF5 and a test substance, and
(iii) culturing the cells obtained by step (ii) in suspension culture in a medium containing ascorbic acid, BMP2, TGFβ, GDF5 and the test substance.

[12] The method of the above [10] or [11], wherein the chondrocyte marker gene is one or more genes selected from the group consisting of SOX9, AGGRECAN and COL2.

[13] The method of the above [10] or [11], wherein the fibroblast marker gene is COL1A1 and/or COL1A2.

[14] The method of any one of the above [10] to [13], wherein the FGFR3 mutation is Arg248Cys or Gly380Arg mutation in FGFR3.

[15] The method of any one of the above [10] to [14], wherein the FGFR3 disease is thanatophoric dysplasia (TD) and/or achondroplasia (ACH).

[16] A HMG-CoA reductase inhibitor for use in the treatment and/or prevention of a FGFR3 disease.

[17] The HMG-CoA reductase inhibitor for use of the above [16], which is a drug selected from the group consisting of mevastatin, atorvastatin, pravastatin, rosuvastatin, fluvastatin and lovastatin.

[18] The HMG-CoA reductase inhibitor for use of the above [17] or [18], wherein the FGFR3 disease is thanatophoric dysplasia (TD) and/or achondroplasia (ACH).

Advantageous Effects of Invention

The present invention provides a novel tool for screening for a therapeutic and/or prophylactic agent for FGFR3 diseases. The present invention also provides a therapeutic and/or prophylactic agent for FGFR3 diseases, the agent being identified by the screening.

BRIEF DESCRIPTION OF DRAWINGS

In FIG. 1A, the left panel shows a phase contrast image of TD-iPSCs (TD714-3), and the right panels show the fluorescence images of TD-iPSCs (TD714-3) for SSEA4 and TRA1-60. The scale bar is 50 μm. FIG. 1B shows the histology of teratomas formed after implantation of TD-iPSCs (TD10749-2) into SCID mice. The scale bar is 50 μm.

FIGS. 2A and 2B show the chondrogenic differentiation of TD-iPSCs and WT-iPSCs. FIG. 2A shows the histology of particles on day 42 that were chondrogenically differentiated from iPSC lines. The scale bar is 50 μm. HE indicates hematoxylin and eosin staining, and Safranin O indicates safranin O-fast green-iron hematoxylin staining. FIG. 2B shows the number of particles that were substantially positively stained by safranin O out of arbitrary selected ten particles differentiated from each iPSC line. All the particles generated from WT-iPSC lines contained cartilaginous tissue, whereas none of the particles generated from TD-iPSC lines contained cartilaginous tissue.

FIG. 3A shows the results of real-time RT-PCR expression analysis of chondrocyte marker genes (SOX9, COL2 and AGGRECAN) and fibroblast marker genes (COL1A1 and COL1A2) on day 28 of chondrogenic differentiation from iPSC lines. FIG. 3B shows the immunohistology of the iPSC-derived chondrocytes on day 42 of differentiation. The scale bar is 50 μm. FIG. 3C shows the immunostaining of type II collagen in the cartilaginous particles derived from TD-iPSCs (TD-714-3) and WT-iPSCs (409B2).

FIG. 4A shows the results of real-time RT-PCR expression analysis of FGFR3 mRNA in the chondrogenic differentiation of TD-iPSCs and WT-iPSCs. Human fetal chondrocytes purchased from Cell Applications, Inc. (402RD-R10f) are shown as a positive control (Chondrocyte), and fibroblasts are shown as a negative control (Fibroblast). FIG. 4B shows the results of quantitative PCR analysis of the expression level of FGFR3 mRNA in chondrogenically differentiated TD-iPSCs and WT-iPSCs on day 28. The mean of three TD-iPSC lines were compared with the means of three WT-iPSC lines by t-test (*$p<0.05$). FIG. 4C shows the results of immunoblot analysis of FGFR3 protein in chondrogenically differentiated TD-iPSCs and WT-iPSCs on day 28. FIG. 4D shows the time course of the changes in the expression of marker genes (OCT3/4, T, KDR, SOX5, SOX6, SOX9, COL2A1 and ACAN), as determined by quantitative PCR. The data are the mean of triplicate.

FIG. 5A shows the immunostaining of chondrogenically differentiated TD-iPSCs (TD714-3) and WT-iPSCs (409B2) on day 28 that were treated with BrdU and immunostained with anti-BrdU antibody. FIG. 5B shows the number of BrdU-positive cells. FIG. 5C shows the results of TUNEL assay of the iPSC-derived particles on day 21 of differentiation. The scale bar is 50 m. FIG. 5D shows the ratio of the number of TUNEL-positive cells per the total cell number during the chondrogenic differentiation of TD-iPSCs and WT-iPSCs. FIG. 5E shows the immunostaining of cleaved-caspase 3 in chondrogenically differentiated TD-iPSCs (TD714-3) and WT-iPSCs (40982) on day 28. FIG. 5F shows the results of quantitative PCR expression analysis of p21 in the chondrocytes differentiated from the iPSC lines.

FIG. 6A shows the construct of the FGFR3 shRNA PB vector. FIG. 6B shows the results of immunoblot analysis of 293 cells transduced with one of the shRNA PB vectors targeting three different sites of FGFR3 (shFGFR3 1, shFGFR3 3, and shFGFR3 5), using anti-FGFR3 antibody. FIG. 6C shows the histology of the particles that were chondrogenically differentiated from the TD-iPSC lines transduced with one of the three different FGFR3 shRNAs (shFGFR3 1, shFGFR3 3, and shFGFR3 5) and the negative control shRNA targeting the luciferase sequence (shLuciferase) on day 42 of differentiation. The scale bar is 50 µm. FIG. 6D shows the number of particles that were substantially positively stained by safranin O out of arbitrary selected ten particles differentiated from each of the iPSC lines transduced with one of the FGFR3 shRNAs and shLuciferase. FIG. 6E shows the results of real-time RT-PCR expression analysis of marker genes (SOX9, COL2, AGGRECAN, COL1A1 and COL1A2) in the chondrocytes differentiated from the iPSCs (shFGFR3 1, shFGFR3 3, shFGFR3 5, shLuciferase, and WT-iPSCs (WT)) on day 28, undifferentiated iPSCs, and chondrocytes (Chondrocyte, 402RD-R10f).

FIGS. 7A to 7C show the results of chondrogenic induction from TD-iPSCs (TD714-3) with addition of FGFR3 neutralizing antibody. FIG. 7A shows the histology of particles on day 42 differentiated from TD-iPSCs with addition of FGFR3 neutralizing antibody to the medium during the chondrogenic differentiation of the cells. As a negative control, IgG was added instead of the FGFR3 neutralizing antibody. The scale bar is 50 µm. FIG. 7B shows the number of particles that were substantially positively stained by safranin O out of arbitrary selected three particles differentiated from TD-iPSCs with addition of FGFR3 neutralizing antibody (Anti-FGFR3) or the negative control (IgG). FIG. 7C shows the results of real-time RT-PCR expression analysis of marker genes (SOX9, COL2, AGGRECAN, COL1A1 and COL1A2) in the chondrocytes differentiated from the iPSCs (TD-iPSCs and WT-iPSCs (WT) with addition of Anti-FGFR3 or IgG) on day 28, undifferentiated iPSCs, and chondrocytes (Chondrocyte, 402RD-R10f).

FIGS. 8A to 8C show the results of chondrogenic induction from TD-iPSCs (TD714-3) in the presence of test substances. FIG. 8A shows the histology of particles on day 42 differentiated from TD-iPSCs with addition of test substances to the medium during the chondrogenic differentiation of the cells. The scale bar is 50 µm. FIG. 8B shows the number of particles that were substantially positively stained by safranin O out of arbitrary selected ten particles differentiated from TD-iPSCs with addition of the test substances. FIG. 8C shows the results of quantitative PCR expression analysis of marker genes (SOX9, COL2, AGGRECAN, COL1A1 and COL1A2) in the chondrocytes differentiated from the iPSCs (TD-iPSCs and WT-iPSCs (WT) with addition of a FGF inhibitor (FGFR inh), an IGF1R inhibitor (IGFR inh), CNP, NF449, or vehicle (Vehicle)) on day 28, undifferentiated iPSCs, and chondrocytes (402RD-R10f) (Chondrocyte).

FIGS. 9A to 9C show the results of chondrogenic induction from TD-iPSCs (TD714-3) in the presence of lovastatin. FIG. 9A shows the histology of particles on day 42 differentiated from TD-iPSCs with addition of lovastatin to the medium during the chondrogenic differentiation of the cells. The scale bar is 50 µm. FIG. 9B shows the number of particles that were substantially positively stained by safranin O out of arbitrary selected ten particles differentiated from TD-iPSCs with addition of lovastatin or vehicle. FIG. 9C shows the results of quantitative PCR expression analysis of marker genes (SOX9, COL2, AGGRECAN, COL1A1 and COL1A2) in the chondrocytes differentiated from the iPSCs (TD-iPSCs and WT-iPSCs (WT) with addition of lovastatin (Lova) or vehicle (Vehicle)) on day 28, undifferentiated iPSCs, and chondrocytes (402RD-R10f) (Chondrocyte).

FIG. 10A shows the immunostaining of TD-iPSCs that were differentiated in the presence or absence of lovastatin, treated with BrdU on day 28 and immunostained with anti-BrdU antibody. The scale bar is 50 µm. FIG. 10B shows the number of BrdU-positive cells. FIG. 10C shows the safranin O staining of chondrogenically differentiated TD-iPS-derived particles with addition of statins (mevastatin, atorvastatin, pravastatin, rosuvastatin, and fluvastatin) and vehicle (Vehicle) on day 42. The scale bar is 50 µm. FIG. 10D shows the area of the safranin O-positive region relative to the total area of the particle. FIG. 10E shows the results of immunoblot analysis of WT-iPSCs, TD-iPSCs, and lovastatin-treated TD-iPSCs on day 28 of differentiation and 293FT cells, using FGFR3 antibody and phosphorylated MAPK antibody.

FIG. 11A shows the histology of particles on day 42 differentiated from ACH-iPSCs with addition of vehicle (Vehicle), lovastatin or CNP to the medium during the chondrogenic differentiation of the cells. The scale bar is 50 µm. FIG. 11B shows the number of particles that were substantially positively stained by safranin O out of arbitrary selected three particles differentiated from TD-iPSCs with addition of lovastatin, CNP or vehicle (Vehicle).

FIG. 12A shows X-ray images of the heads in lateral views, X-ray images of the bodies in anterior-posterior views, and X-ray images of the hindlimbs. The scale bar is 2 mm. FIG. 12B shows the results of measurements of the anteroposterior length of the heads (Cranial A-P), the length of the ulnas (Ulna), the length of the femurs (Femur) and the length of the tibiae (Tibia). The data were compared by t-test.

FIG. 14A shows the appearance and X-ray images of the bodies of the mice. FIG. 14B shows the X-ray images of the hindlimb skeletons. FIG. 14C shows the appearance and X-ray images of the heads of the mice. Lateral views. FIG. 14D shows the appearance and X-ray images of the heads of the mice. Anterior-posterior views.

FIG. 16A shows the images of the metatarsal primordial cartilages in organ culture on day 7. FIG. 16B shows the results of measurements of the lengths of the primordial cartilages on days 1 and 7 of organ culture. FIG. 16C shows the metatarsal primordial cartilages treated with BrdU and immunostained with BrdU antibody or stained with safranin O on day 7 of organ culture. FIG. 16D shows the number of BrdU-positive cells in the total cells. FIG. 16E shows the safranin O staining of pellets cultured for 14 days. FIG. 16F shows the results of quantitative PCR expression analysis of pellets cultured for 14 days (Sox9, Col2a1 and Acan) and 28 days (Runx2 and Col10a1). FIG. 16G shows the results of immunoblot analysis of wild-type or FGFR3$^{Ach}$ mouse-derived primary chondrocytes cultured in the presence of lovastatin, MG132 or Bafilomycun A1 (Baf A1), using FGFR3 antibody.

DESCRIPTION OF EMBODIMENTS

Figure 1A:
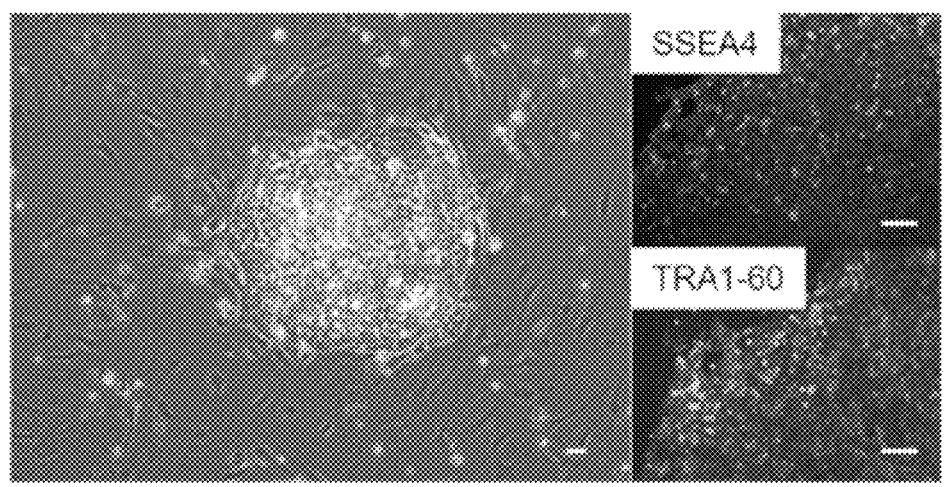
FIGS. 1A and 1B show the characterization of TD-iPSCs.

The term "FGFR3 diseases" herein means any types of osteogenic disorders involving abnormal bone formation due to FGFR3 mutations. FGFR3 diseases preferably refer to a group of FGFR3 diseases described in the international classification of skeletal dysplasias (Warman et al., Am J Med Genet 155A(5): 943-68 (2011)), including, for example, thanatophoric dysplasia (TD), achondroplasia (ACH), hypochondroplasia, camptodactyly, tall stature, and hearing loss syndrome (CATSHL), Crouzon-like craniosynostosis with *acanthosis nigricans* (Crouzonodermoskeletal), and craniosynostosis. FGFR3 mutations may be gain-of-function or loss-of-function mutations, but preferred may be gain-of-function mutations.

Generation of iPS Cells

The iPS cells herein can be generated by introducing specific nuclear reprogramming substances in the form of DNA or protein into somatic cells, or by increasing the mRNA or protein expression of endogenous nuclear reprogramming substances by drug treatment. iPS cells are somatic cell-derived artificial stem cells having properties almost equivalent to those of ES cells, such as pluripotency and proliferation potency via self-replication (K. Takahashi and S. Yamanaka (2006) Cell, 126: 663-676, K. Takahashi et al. (2007) Cell, 131: 861-872, J. Yu et al. (2007) Science, 318: 1917-1920, M. Nakagawa et al., (2008) Nat. Biotechnol., 26: 101-106, WO 2007/069666, and WO 2010/068955). The nuclear reprogramming substance may be a gene specifically expressed in ES cells, a gene playing an important role in maintenance of undifferentiation of ES cells, or a gene product thereof. Examples of such nuclear reprogramming substance include, but are not particularly limited to, Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Nanog, Esrrb, Esrrg, and Glis1. These reprogramming substances may be used in combination to establish iPS cells. Such a combination may contain at least one, two or three of the above reprogramming substances, and preferably contains four or five of the above reprogramming substances.

The nucleotide sequence information of mouse or human cDNA of each of the above nuclear reprogramming substances and the amino acid sequence information of a protein encoded by the cDNA can be obtained by referring to the NCBI accession numbers described in WO 2007/069666. The mouse and human cDNA sequence information and amino acid sequence information of L-Myc, Lin28, Lin28b, Esrrb, Esrrg, and Glis1 can be obtained by referring to the NCBI accession numbers described below. A person skilled in the art can prepare the desired nuclear reprogramming substances by a conventional technique based on the cDNA sequence information or the amino acid sequence information.

| Gene name | Mouse | Human |
|---|---|---|
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

The nuclear reprogramming substances may be introduced in the form of protein into somatic cells by a technique such as lipofection, fusion with a cell membrane-permeable peptide, or microinjection. Alternatively, the nuclear reprogramming substances may be introduced in the form of DNA into somatic cells by a technique such as a technique using a vector (such as a viral vector, a plasmid vector and an artificial chromosome vector), lipofection, a technique using a liposome, or microinjection. Examples of the viral vector include retroviral vectors, lentiviral vectors (both described in Cell, 126, pp. 663-676, 2006; Cell, 131, pp. 861-872, 2007; Science, 318, pp. 1917-1920, 2007), adenoviral vectors (Science, 322, 945-949, 2008), adeno-associated viral vectors, and Sendai virus vectors (Proc Jpn Acad Ser B Phys Biol Sci. 85, 348-62, 2009). Examples of the artificial chromosome vectors include human artificial chromosome (HAC) vectors, yeast artificial chromosome (YAC) vectors, and bacterial artificial chromosome (BAC, PAC) vectors. Examples of the plasmid vectors include plasmids for mammalian cells (Science, 322: 949-953, 2008). Such a vector can contain regulatory sequences such as a promoter, an enhancer, a ribosome binding sequence, a terminator, and a polyadenylation site, so that a nuclear reprogramming substance can be expressed. Examples of the promoter to be used herein include an EF1α promoter, a CAG promoter, an SRα promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Preferred are an EF1α promoter, a CAG promoter, MoMuLV LTR, a CMV promoter, and an SRα promoter. The vector may further contain, if necessary, a selection marker sequence such as a drug resistance gene (e.g., a kanamycin resistance gene, an ampicillin resistance gene, and a puromycin resistance gene), a thymidine kinase gene, and a diphtheria toxin gene, and a reporter gene sequence such as a green fluorescent protein (GFP), β-glucuronidase (GUS), and FLAG. In order to remove a gene encoding a nuclear reprogramming substance or remove a promoter together with a gene encoding a nuclear reprogramming substance binding thereto after introduction of the vector into somatic cells, LoxP sequences may be inserted upstream and downstream of the region to be removed. In another preferred embodiment, a transposon system can be used in which a transgene is inserted into a chromosome by a transposon and then the cells are transfected with a transferase via a plasmid vector or an adenoviral vector to completely remove the transgene from the chromosome. Examples of preferred transposons include the lepidopteran-derived transposon piggyBac (Kaji, K. et al., (2009), Nature, 458: 771-775, Woltjen et al., (2009), Nature, 458: 766-770, WO 2010/012077). The vector used in the present invention may also contain the replication origin and the replication-related sequence of a lymphotropic herpes virus, BK virus, or Bovine papilloma virus, so that the vector replicates itself even without being incorporated into a chromosome and is episomally present. For example, the vector may contain EBNA-1 and oriP sequences, or Large T and SV40ori sequences (WO 2009/115295, WO 2009/157201, and WO 2009/149233). Polycistronic expression vectors may also be used to simultaneously introduce a plurality of nuclear reprogramming substances. For polycistronic expression, the sequences encoding the genes may be linked via an IRES or a foot and mouth disease virus (FMDV) 2A coding region (Science, 322: 949-953, 2008, WO 2009/092042 and WO 2009/152529).

In addition to the above factors, other factors may also be used for nuclear reprogramming to enhance the efficiency of induction of iPS cells, and examples of such factors include histone deacetylase (HDAC) inhibitors [e.g., low-molecular-weight inhibitors, such as valproic acid (VPA) (Nat. Biotechnol., 26(7): 795-797 (2008)), trichostatin A, sodium butyrate, MC 1293, and M344, and nucleic acid-based expression inhibitors such as siRNA and shRNA against HDAC (e.g., HDAC1 siRNA Smartpool (registered trademark) (Millipore) and HuSH 29-mer shRNA Constructs against HDAC1 (OriGene))], DNA methyltransferase inhibitors (e.g., 5'-azacytidine) (Nat. Biotechnol., 26(7): 795-797 (2008)), G9a histone methyltransferase inhibitors [e.g., low-molecular-weight inhibitors such as BIX-01294 (Cell Stem Cell, 2: 525-528 (2008)) and nucleic acid-based expression inhibitors such as siRNA and shRNA against G9a (e.g., G9a siRNA (human) (Santa Cruz Biotechnology))], L-channel calcium agonists (e.g., Bayk8644) (Cell Stem Cell, 3, 568-574 (2008)), p53 inhibitors (e.g., siRNA and shRNA against p53) (Cell Stem Cell, 3, 475-479 (2008)), Wnt signaling activators (e.g., soluble Wnt3a) (Cell Stem Cell, 3, 132-135 (2008)), growth factors such as LIF or bFGF, ALK5 inhibitors (e.g., SB431542) (Nat Methods, 6: 805-8 (2009)), mitogen-activated protein kinase signaling inhibitors, glycogen synthase kinase-3 inhibitors (PloS Biology, 6(10), 2237-2247 (2008)), miRNAs such as miR-291-3p, miR-294, and miR-295 (R. L. Judson et al., Nat. Biotech., 27: 459-461 (2009)).

The iPS cells herein may be generated by increasing the protein expression of endogenous nuclear reprogramming substances by drug treatment. Examples of the drug include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

A culture medium for iPS cell induction includes, for example, (1) DMEM, DMEM/F12, or DME medium containing 10 to 15% FBS (these media may further contain LIF, penicillin/streptomycin, puromycin, L-glutamine, nonessential amino acids, α-mercaptoethanol, etc. as needed), (2) a medium for ES cell culture containing bFGF or SCF, for example, a medium for mouse ES cell culture (e.g., TX-WES medium (Thromb-X)), a medium for primate ES cell culture (e.g., a medium for primate (humans and monkeys) ES cells (ReproCELL, Kyoto, Japan), mTeSR-1), etc.

An exemplary culture method is as follows. Somatic cells are brought into contact with nuclear reprogramming substances (DNAs or proteins) in a DMEM or DMEM/F12 medium containing 10% FBS at 37° C. in an atmosphere of 5% $CO_2$ and are cultured for about 4 to 7 days. The cells are then reseeded on feeder cells (e.g., mitomycin C-treated STO cells or SNL cells). About 10 days after contact between the somatic cells and the nuclear reprogramming substances, the cells are subjected to culture in a bFGF-containing medium for primate ES cell culture. About 30 to 45 days or more after the contact, ES cell-like colonies appear. In order to enhance the efficiency of induction of iPS cells, the somatic cells may be cultured under low oxygen conditions of 5 to 10%. Instead of feeder cells, an extracellular matrix may be used. Examples of the extracellular matrix include collagens, gelatins, laminins (e.g., laminin 111, 411 or 511, or fragments thereof), heparan sulfate proteoglycan, entactins, fragments thereof, and combinations thereof.

Alternatively, the somatic cells are cultured on feeder cells (e.g., mitomycin C-treated STO cells, SNL cells, etc.) in a 10% FBS-containing DMEM medium (this media may further contain LIF, penicillin/streptomycin, puromycin, L-glutamine, nonessential amino acids, β-mercaptoethanol, etc. as needed). About 25 to 30 days or more after the start of culture, ES-like colonies appear.

During the above culture, medium exchange with a fresh medium is performed once a day from day 2 after the start of culture. The number of somatic cells to undergo nuclear reprogramming is not limited, but, for example, ranges from about $5 \times 10^3$ to about $5 \times 10^6$ cells per culture dish (100 cm$^2$).

When a gene containing a drug resistance gene is used as a marker gene, marker gene-expressing cells can be selected by culturing the cells in a medium containing the relevant drug (selective medium). When a fluorescent protein gene is used as a marker gene, marker gene-expressing cells can be detected by observation under a fluorescence microscope. When a luminescent enzyme gene is used as a marker gene, marker gene-expressing cells can be detected by adding a luminescent substrate. When a chromogenic enzyme gene is used as a marker gene, marker gene-expressing cells can be detected by adding a chromogenic substrate.

The term "somatic cells" as used herein refers to any types of animal cells (e.g., human, mouse, monkey, pig, or rat cells, etc.) other than germ cells. Examples of the somatic cells include keratinizing epithelial cells (e.g., keratinizing epidermal cells), mucosal epithelial cells (e.g., epithelial cells on the surface layer of the tongue), exocrine epithelial cells (e.g., mammary glandular cells), hormone-secreting cells (e.g., adrenal medulla cells), metabolism and storage cells (e.g., hepatocytes), boundary-forming luminal epithelial cells (e.g., type I alveolar cells), luminal epithelial cells of the closed circulatory system (e.g., vascular endothelial cells), ciliated cells with propulsive function (e.g., airway epithelial cells), extracellular matrix-secreting cells (e.g., fibroblasts), contractile cells (e.g., smooth muscle cells), blood and immune system cells (e.g., T lymphocytes, non-T lymphocytes), sensory cells (e.g., rod cells), autonomic nervous system neurons (e.g., cholinergic neurons), supporting cells in the sense organ and the peripheral nervous system (e.g., satellite cells), nerve cells and glial cells in the central nervous system (e.g., astroglial cells), pigment cells (e.g., retinal pigment epithelial cells), and progenitor cells therefor (tissue progenitor cells). There is no particular limitation for the degree of cell differentiation, the age of an animal as a cell source, etc. Undifferentiated progenitor cells (including somatic stem cells) as well as terminally differentiated mature cells can be used as the source of somatic cells in the present invention. Examples of the undifferentiated progenitor cells include tissue stem cells (somatic stem cells) such as neural stem cells, hematopoietic stem cells, mesenchymal stem cells, and dental pulp stem cells. For the production of iPS cells derived from FGFR3 disease patients in the present invention, preferred are hemocytes or fibroblasts, and particularly preferred are human dermal fibroblasts (HDFs).

A mammal that serves as the source of the somatic cells is not particularly limited herein, but preferred is a human.

The iPS cells herein generated from the somatic cells of a subject with a FGFR3 disease may have a FGFR3 gene mutation specific to FGFR3 disease patients. Examples of the mutation specific to FGFR3 disease patients include Arg246Cys, Arg248Cys, Ser249Cys, Gly370Cys, Ser371Cys, Thr373Cys, Lys650Glu, X807Arg, X807Cys, etc. in the case of TD, and Gly380Arg, Gly375Cys, etc. in the case of ACH, but the mutation is not limited thereto.

Method for Inducing Differentiation Toward Chondrocytes

Induction of differentiation of the iPS cells into chondrocytes may be achieved by any method in the art. The method for inducing the differentiation may be those known to a person skilled in the art at the time of filing of the present application as well as those developed after the filing of the present application. Examples of the method for inducing differentiation toward chondrocytes include, but are not limited to, those described in Koyama, N. et al. Stem cells and development 22, 102-113 (2013), Hwang, N. S., et al. PLoS ONE 3, e2498 (2008), Oldershaw, R. A. et al. Nat. Biotechnol. 28, 1187-1194 (2010), Bai, H. Y., et al. Journal of biomedical materials research. Part A 94, 539-546 (2010), and Yamashita, A. et al. Scientific Reports 3 (2013).

The term "chondrocytes" used herein refers to cells that produce an extracellular matrix (such as collagen) that forms cartilage, or refers to progenitor cells of such cells. The chondrocytes may be cells expressing a chondrocyte marker, for example, type II collagen (COL2A1), SOX9 or AGGRECAN. The COL2A1 herein includes human COL2A1 genes having nucleotide sequences of NCBI accession numbers NM_001844 and NM_033150, mouse COL2A1 genes having nucleotide sequences of NCBI accession numbers NM 001113515 and NM_031163, proteins encoded by the genes, and naturally occurring variants having the same functions as those of the genes or the proteins. The SOX9 herein includes a human SOX9 gene having a nucleotide sequence of NCBI accession number NM_000346, a mouse SOX9 gene having a nucleotide sequence of NCBI accession number NM_011448, proteins encoded by the genes, and naturally occurring variants having the same functions as those of the genes or the proteins. The AGGRECAN herein includes human AGGRECAN genes having nucleotide sequences of NCBI accession numbers NM_001135 and NM_013227, a mouse AGGRECAN gene having a nucleotide sequence of NCBI accession number NM_007424, proteins encoded by the genes, and naturally occurring variants having the same functions as those of the genes or the proteins. The cartilaginous extracellular matrix herein is an extracellular matrix that is positively stained by safranin O and its analogs. The chondrocytes in the present invention may be preferably in the form of cultured cells embedded in the extracellular matrix produced by the chondrocytes (i.e., may be cartilaginous tissue in the form of particles).

Induction of differentiation toward chondrocytes is achieved in accordance with, for example, the protocol described below (Oldershaw, R. A. et al. Nat. Biotechnol. 28, 1187-1194 (2010)), using an appropriately selected differentiation-inducing factor. Examples of the differentiation-inducing factor used herein include, but are not limited to, Wnt3A, Activin, FGF2, BMP4, Follistatin, GDF5, and NT4. These factors may be added in any appropriate combination at any appropriate step of the culture process for differentiation toward chondrocytes. A preferred culture process comprises the steps of, for example, (1) culturing iPS cells in a basal medium supplemented with Wnt3A, Activin and FGF2, (2) culturing the cells obtained by step (1) in a basal medium supplemented with FGF2, BMP4, Follistatin and NT4, and (3) culturing the cells obtained by step (2) in a basal medium supplemented with FGF2, BMP4, GDF5 and NT4. Through the culture process, the cells may be cultured as an adherent layer in a culture vessel, or as free-floating cells in a medium. The adherent culture may be performed in a culture vessel coated with, for example, Matrigel (BD), type I collagen, type IV collagen, gelatin, laminin, heparan sulfate proteoglycan, entactin, or a combination thereof.

Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, sodium selenite, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM/F12 containing insulin, transferrin, sodium selenite, and 1% serum.

The concentration of Wnt in the basal medium is, for example, in the range of 1 to 200 ng/ml, preferably in the range of 10 to 50 ng/ml, and is, for example, 1 ng/ml, 10 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, or 200 ng/ml, but is not limited thereto. Preferably, the concentration is 25 ng/ml.

The concentration of Activin in the basal medium is, for example, in the range of 1 to 200 ng/ml, preferably in the range of 10 to 50 ng/ml, and is, for example, 1 ng/ml, 10 ng/ml, 20 ng/ml, 25 ng/ml, 30 ng/ml, 40 ng/ml, 50 ng/ml, 60 ng/ml, 70 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, or 200 ng/ml, but is not limited thereto. Preferably, the concentration is 25 ng/ml. The concentration of Activin in the medium can be changed during the culture period. For example, after the cells are cultured with Activin at 50 ng/ml for one day, the concentration is changed to 25 ng/ml and the cells are cultured for one day, and then the concentration is changed to 10 ng/ml and the cells are cultured for one day.

The concentration of FGF2 in the basal medium is, for example, in the range of 1 to 100 ng/ml, preferably in the range of 20 to 40 ng/ml, and is, for example, 1 ng/ml, 10 ng/ml, 15 ng/ml, 20 ng/ml, 25 ng/ml, 30 ng/ml, 40 ng/ml, 50 ng/ml, 60 ng/ml, 70 ng/ml, 80 ng/ml, 90 ng/ml, or 100 ng/ml, but is not limited thereto. Preferably, the concentration is 20 ng/ml.

The concentration of BMP4 in the basal medium is, for example, in the range of 1 to 100 ng/ml, preferably in the range of 20 to 40 ng/ml, and is, for example, 1 ng/ml, 10 ng/ml, 20 ng/ml, 25 ng/ml, 30 ng/ml, 35 ng/ml, 40 ng/ml, 50 ng/ml, 60 ng/ml, 70 ng/ml, 80 ng/ml, 90 ng/ml, or 100 ng/ml, but is not limited thereto. Preferably, the concentration is 40 ng/ml. The concentration of BMP4 in the medium can be changed during the culture period. For example, after the cells are cultured with BMP4 at 40 ng/ml for six days, the concentration is changed to 25 ng/ml and the cells are cultured for two days.

The concentration of Follistatin in the basal medium is, for example, in the range of 1 to 200 ng/ml, preferably in the range of 50 to 150 ng/ml, and is, for example, 1 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, or 200 ng/ml, but is not limited thereto. Preferably, the concentration is 100 ng/ml.

The concentration of GDF5 in the basal medium is, for example, in the range of 1 to 100 ng/ml, preferably in the range of 20 to 40 ng/ml, and is, for example, 1 ng/ml, 10 ng/ml, 20 ng/ml, 25 ng/ml, 30 ng/ml, 35 ng/ml, 40 ng/ml, 50 ng/ml, 60 ng/ml, 70 ng/ml, 80 ng/ml, 90 ng/ml, or 100 ng/ml, but is not limited thereto. Preferably, the concentration is 40 ng/ml. The concentration of GDF5 in the medium can be changed during the culture period. For example, after the cells are cultured with GDF5 at 20 ng/ml for two days, the concentration is changed to 40 ng/ml and the cells are cultured for three days.

The concentration of NT4 in the basal medium is, for example, in the range of 1 to 10 ng/ml, preferably in the range of 1 to 5 ng/ml, and is, for example, 1 ng/ml, 1.5 ng/ml, 2 ng/ml, 2.5 ng/ml, 3 ng/ml, 4 ng/ml, 5 ng/ml, 6 ng/ml, 7 ng/ml, 8 ng/ml, 9 ng/ml, or 10 ng/ml, but is not limited thereto. Preferably, the concentration is 2 ng/ml.

Preferably, in the present invention, the induction of chondrocytes from the iPS cells is achieved by a modified method comprising the steps of:
(i) inducing mesodermal cells from iPS cells in adherent culture,
(ii) culturing the cells obtained by step (i) in adherent culture in a medium containing bFGF, ascorbic acid, BMP2, TGFβ and GDF5, and
(iii) culturing the cells obtained by step (ii) in suspension culture in a medium containing ascorbic acid, BMP2, TGFβ and GDF5.

(i) Step of Inducing Mesodermal Cells from iPS Cells in Adherent Culture

The term "mesodermal cells" herein refers to cells that occur between the endoderm and the ectoderm at the gastrula stage of animal development, and are preferably BRACHYURY positive. The BRACHYURY herein includes human BRACHYURY genes having nucleotide sequences of NCBI accession numbers NM_001270484 and NM_003181, a mouse BRACHYURY gene having a nucleotide sequence of NCBI accession number NM_009309, proteins encoded by the genes, and naturally occurring variants having the same functions as those of the genes or the proteins.

According to the present invention, the induction of mesodermal cells from iPS cells may be achieved by any method, and, for example, is achieved by culturing iPS cells in a medium containing Activin A and a GSK-3β inhibitor.

Preferably, in step (i), iPS cells are cultured in adherent culture without feeder cells. After the cell colonies reach an appropriate size (cell nodules each containing $1 \times 10^5$ to $2 \times 10^5$ cells), the medium is exchanged with a medium containing Activin A and a GSK-3β inhibitor, and culture is continued.

The adherent culture herein may be culture in a culture vessel coated with an extracellular matrix. The coating may be applied by adding a solution containing an extracellular matrix to a culture vessel, followed by appropriately removing the solution.

The extracellular matrix herein is a supramolecular assembly present outside the cells, and may be naturally occurring or artificial (recombinant). Examples of the extracellular matrix include collagens, proteoglycans, fibronectins, hyaluronic acid, tenascins, entactins, elastin, fibrillins, laminins, and fragments of these substances. These extracellular matrices may be used in combination. The extracellular matrix may be a product prepared using cells, such as BD Matrigel™. Examples of the artificial extracellular matrix include laminin fragments. The laminins herein are hetero-trimeric proteins that contain an α-chain, a β-chain and a γ-chain, and are not particularly limited in the present invention. For example, the α-chain is α1, α2, α3, α4, or α5, the β chain is β1, β2, or β3, and the γ chain is γ1, γ2, or γ3. The laminin fragments herein are not particularly limited as long as they have integrin-binding activity, and examples thereof include laminin E8 fragments produced by digesting laminins with elastase.

The medium used in step (i) may be prepared by adding Activin A and a GSK-3β inhibitor to a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, sodium selenite, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM/F12 containing insulin, transferrin, sodium selenite and 1% serum.

The Activin A in step (i) includes Activin A derived from an animal such as a human and a non-human animal and functionally modified derivatives thereof. The Activin A may be, for example, a commercially available product produced by R&D systems etc. The concentration of Activin A used in this step is 0.1 to 1000 ng/ml, preferably 1 to 100 ng/ml, more preferably 5 to 50 ng/ml, and further preferably 10 ng/ml.

The GSK-3β inhibitor in step (i) is not particularly limited as long as it directly or indirectly inhibits the functions of GSK-3β, for example, kinase activity. Examples of the GSK-3β inhibitor include Wnt3a, the indirubin derivative BIO (also called GSK-3β inhibitor IX (6-bromoindirubin-3'-oxime)), the maleimide derivative SB216763 (3-(2,4-dichlorophenyl)-4-(1-methyl-1H-indol-3-yl)-1H-pyrrole-2,5-dione), the phenyl α-bromomethyl ketone compound GSK-3β inhibitor VII (4-dibromoacetophenone), the cell membrane-permeable phosphopeptide L803-mts (also called GSK-3β peptide inhibitor (Myr-N-GKEAPPAP-PQSpP-NH2)) and the highly selective inhibitor CHIR99021 (Nature (2008) 453: 519-523). These compounds are commercially available from, for example, Stemgent, Calbiochem, Biomol, etc., or may be produced in-house. A preferred GSK-3β inhibitor used in this step is Wnt3a. The Wnt3a includes Wnt3a derived from an animal such as a human and a non-human animal and functionally modified derivatives thereof. The Wnt3a may be, for example, a commercially available product produced by R&D systems etc. The concentration of the GSK-3β inhibitor used in this step may be selected by a person skilled in the art as appropriate for the type of the GSK-3β inhibitor to be used. For example, the concentration of Wnt3a used as the GSK-3β inhibitor is 0.1 to 1000 ng/ml, preferably 1 to 100 ng/ml, more preferably 5 to 50 ng/ml, and further preferably 10 ng/ml.

The culture temperature in step (i) is not particularly limited, but, for example, ranges from about 30° C. to about 40° C., and is preferably about 37° C. The culture is performed under an air atmosphere containing $CO_2$. The $CO_2$ concentration ranges from about 2% to 5%, and is preferably about 5%. The culture period in this step is, for example, 5 days or less, and is preferably 3 days.

(ii) Step of Culturing the Cells Obtained by Step (i) in Adherent Culture in a Medium Containing bFGF, Ascorbic Acid, BMP2, TGFβ and GDF5

In this step, the medium of the cell culture in step (i) is removed and exchanged with a medium containing bFGF, ascorbic acid, BMP2, TGFβ and GDF5. The cells in the culture in step (i) are adherent to culture dishes, and the adherent culture is continued in step (ii).

The medium used in step (ii) may be prepared by adding bFGF, ascorbic acid, BMP2, TGFβ and GDF5 to a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing insulin, transferrin, sodium selenite, and 1% serum.

The bFGF in step (ii) includes bFGF derived from an animal such as a human and a non-human animal and functionally modified derivatives thereof. The bFGF may be, for example, a commercially available product produced by WAKO etc. The concentration of bFGF used in this step is 0.1 to 1000 ng/ml, preferably 1 to 100 ng/ml, more preferably 5 to 50 ng/ml, and further preferably 10 ng/ml.

The ascorbic acid in step (ii) may be, for example, a commercially available product produced by Nakarai etc. The concentration of the ascorbic acid used in this step is 5 to 500 μg/ml, preferably 10 to 100 μg/ml, and more preferably 50 μg/ml.

The BMP2 in step (ii) includes BMP2 derived from an animal such as a human and a non-human animal and functionally modified derivatives thereof. The BMP2 may be, for example, a commercially available product produced by Osteopharma etc. The concentration of BMP2 used in this step is 0.1 to 1000 ng/ml, preferably 1 to 100 ng/ml, more preferably 5 to 50 ng/ml, and further preferably 10 ng/ml.

The TGFβ in step (ii) includes TGFβ derived from an animal such as a human and a non-human animal and functionally modified derivatives thereof. The TGFβ may be, for example, a commercially available product produced by PeproTech etc. The concentration of TGFβ used in this step is 0.1 to 1000 ng/ml, preferably 1 to 100 ng/ml, more preferably 5 to 50 ng/ml, and further preferably 10 ng/ml.

The GDF5 in step (ii) includes GDF5 derived from an animal such as a human and a non-human animal and functionally modified derivatives thereof. The GDF5 may be, for example, a commercially available product produced by PeproTech etc. The concentration of GDF5 used in this step is 0.1 to 1000 ng/ml, preferably 1 to 100 ng/ml, more preferably 5 to 50 ng/ml, and further preferably 10 ng/ml.

The culture temperature in step (ii) is not particularly limited, but, for example, ranges from about 30° C. to about 40° C., and is preferably about 37-C. The culture is performed under an air atmosphere containing $CO_2$. The $CO_2$ concentration ranges from about 2% to 5%, and is preferably about 5%. The culture period in this step is, for example, 15 days or less, and is preferably 11 days.

(iii) Step of Culturing the Cells Obtained by Step (ii) in Suspension Culture in a Medium Containing Ascorbic Acid, BMP2, TGFβ and GDF5

In this step, the cells obtained in the culture in step (ii) are separated from the culture dishes and then subjected to suspension culture. The separation of the cells from the culture dishes in step (iii) is preferably achieved by mechanical means (pipetting etc.), not using a detachment solution with protease activity and/or collagenase activity (e.g., solutions containing trypsin and collagenase, such as Accutase™ and Accumax™ (Innovative Cell Technologies, Inc.)).

The term "suspension culture" herein refers to culture of cells that are in a state of being non-adherent to a culture dish. The conditions of the suspension culture are not particularly limited, but preferably the suspension culture is performed in a culture vessel without artificial treatment for enhancing the cell adhesion to the vessel (e.g., without coating treatment using an extracellular matrix etc.) or a culture vessel with artificial treatment for preventing the cell adhesion to the vessel (e.g., with coating treatment using polyhydroxyethyl methacrylate (poly-HEMA)).

The medium used in step (iii) may be prepared by adding ascorbic acid, BMP2, TGFβ and GDF5 to a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing insulin, transferrin, sodium selenite, and 1% serum.

The ascorbic acid in step (iii) may be, for example, a commercially available product produced by Nakarai etc. The concentration of the ascorbic acid used in this step is 5 to 500 μg/ml, preferably 10 to 100 μg/ml, and more preferably 50 μg/ml.

The BMP2 in step (iii) includes BMP2 derived from an animal such as a human and a non-human animal and functionally modified derivatives thereof. The BMP2 may be, for example, a commercially available product produced by Osteopharma etc. The concentration of BMP2 used in this step is 0.1 to 1000 ng/ml, preferably 1 to 100 ng/ml, more preferably 5 to 50 ng/ml, and further preferably 10 ng/ml.

The TGFβ in step (iii) includes TGF derived from an animal such as a human and a non-human animal and functionally modified derivatives thereof. The TGFβ may be, for example, a commercially available product produced by PeproTech etc. The concentration of TGFβ used in this step is 0.1 to 1000 ng/ml, preferably 1 to 100 ng/ml, more preferably 5 to 50 ng/ml, and further preferably 10 ng/ml.

The GDF5 in step (iii) includes GDF5 derived from an animal such as a human and a non-human animal and functionally modified derivatives thereof. The GDF5 may be, for example, a commercially available product produced by PeproTech etc. The concentration of GDF5 used in this step is 0.1 to 1000 ng/ml, preferably 1 to 100 ng/ml, more preferably 5 to 50 ng/ml, and further preferably 10 ng/ml.

The culture temperature in step (iii) is not particularly limited, but, for example, ranges from about 30° C. to about 40-C, and is preferably about 37° C. The culture is performed under an air atmosphere containing $CO_2$. The CO: concentration ranges from about 2% to 5%, and is preferably about 5%. The culture period in this step is, for example, 10 to 30 days, and is preferably 14 to 28 days.

(iv) Step of Further Culturing the Cells Obtained by Step (iii) in Suspension Culture Chondrocytes are obtained at the end of step (iii), but in order to obtain more mature chondrocytes, the cells obtained in the culture in step (iii) may be further cultured in suspension culture.

The medium used in step (iv) is a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing 10% serum.

The culture temperature in step (iv) is not particularly limited, but, for example, ranges from about 30° C. to about 40° C., and is preferably about 37° C. The culture is performed under an air atmosphere containing $CO_2$. The CO concentration ranges from about 2% to 5%, and is preferably about 5%. A longer culture period in this step causes no problems on the production of chondrocytes, and hence the culture period is, for example, 20 days or more, and is preferably 28 days or more.

Preferably, after step (iii) or (iv), the floating cells are selectively isolated as chondrocytes. The chondrocytes generated by the method of the present invention are mostly present as the floating cells in the medium, and thus preferably the floating cells are isolated by selectively excluding the cells adherent to the culture vessel.

Screening Method for Therapeutic and/or Prophylactic Drugs for FGFR3 Diseases

The present invention provides a method for screening for a therapeutic and/or prophylactic drug for FGFR3 diseases, the method comprising bringing the iPS cells generated as described above in contact with a test substance, and analyzing various types of indicators.

In one embodiment of the present invention, a therapeutic and/or prophylactic drug for FGFR3 diseases can be screened by a method comprising the steps of:

(a) differentiating induced pluripotent stem (iPS) cells generated from somatic cells of a subject with a FGFR3 disease into chondrocytes under conditions where the cells are in contact with a test substance and under conditions where the cells are not in contact with the test substance, (b) measuring one or more indicators selected from the group consisting of the amount of cartilaginous extracellular matrix, the expression level of a chondrocyte marker gene, and the expression level of a fibroblast marker gene in cultures resulting from step (a), and (c) identifying the test substance as a therapeutic or prophylactic drug for the FGFR3 disease when the chondrocytes differentiated in contact with the test substance show an increased amount of the cartilaginous extracellular matrix, an increased expression level of the chondrocyte marker gene, or a decreased expression level of the fibroblast marker gene, as compared with the chondrocytes differentiated not in contact with the test substance.

Step (a) corresponds to the above-described process for inducing differentiation toward chondrocytes. The test substance may be brought into contact with the cells through all the steps, but is preferably brought into contact with the cells in steps (2) and/or (3). Alternatively, the test substance may be brought into contact with the cells in steps (ii) and/or (iii), but is more preferably brought into contact with the cells in steps (ii) and (iii).

The iPS cells used herein generated from the somatic cells of a subject with a FGFR3 disease may have a FGFR3 gene mutation specific to FGFR3 disease patients. Examples of the mutation specific to FGFR3 disease patients include Arg246Cys, Arg248Cys, Ser249Cys, Gly370Cys, Ser371Cys, Thr373Cys, Lys650Glu, X807Arg, X807Cys, etc. in the case of TD, and Gly380Arg, Gly375Cys, etc. in the case of ACH, but the mutation is not limited thereto.

The test substances that are to be subjected to the screening method of the present invention may be any types of substances, known compounds or novel compounds. Examples of the test substances include cell extracts, cell culture supernatants, microbial fermentation products, marine organism-derived extracts, plant extracts, purified proteins, crude proteins, peptides, non-peptide compounds, synthetic small molecule compounds, and naturally occurring compounds. The test substances herein can be obtained using any of numerous approaches in combinatorial library methods known in the art, including (1) biological library methods, (2) synthetic library methods requiring deconvolution, (3) the "one-bead one-compound" library method, and (4) synthetic library methods using affinity chromatography selection. The biological library approach using affinity chromatography selection is suited only to peptide libraries, while the other four approaches are applicable to peptide, non-peptide oligomer or small molecule libraries of compounds (Lam (1997) Anticancer Drug Des. 12: 145-67). Examples of synthetic methods of molecular libraries can be found in the art (DeWitt et al. (1993) Proc. Natl. Acad. Sci.

USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). Libraries of compounds may be presented, for example, in solution (see Houghten (1992) Bio/Techniques 13: 412-21), or on beads (Lam (1991) Nature 354: 82-4), chips (Fodor (1993) Nature 364: 555-6), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89: 1865-9), or phages (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; and US Pat. Application 2002103360).

The diseases as targets of the screening method of the present invention may be diseases associated with abnormal bone formation, in particular, FGFR3 diseases. FGFR3 diseases are, for example, in the order of severity, thanatophoric dysplasia (TD), achondroplasia (ACH), hypochondroplasia, but are not limited thereto. Preferred diseases as targets of the screening method of the present invention are thanatophoric dysplasia (TD) and/or achondroplasia (ACH).

The present invention include measurement of the expression levels of marker genes in chondrocytes. Examples of the marker genes include chondrocyte marker genes and fibroblast marker genes. Examples of the chondrocyte marker genes include, but are not limited to, SOX9, AGGRECAN and COL2. Examples of the fibroblast marker genes include, but are not limited to, COL1A1 and COL1A2. In addition to these markers, the amount of chondrocytes can be measured by, for example, staining with antibodies directed to the genes (or proteins) specifically expressed in chondrocytes.

The amount of cartilaginous extracellular matrix herein can be measured by using a substance that specifically stains cartilaginous tissue. Examples of the substance that specifically stains cartilaginous tissue include, but are not limited to, safranin O and its analogs.

Therapeutic and/or Prophylactic Agents for Diseases with FGFR Mutations (e.g., FGFR3 Diseases)

A substance identified by the screening method of the present invention is useful as an active ingredient of a therapeutic and/or prophylactic agent for various chondropathies. The chondropathies as targets of treatment according to the present invention may be any types of chondropathies as long as they can be cured and/or prevented by increasing, through any means, the cartilage volume that has decreased compared with the normal conditions. Examples of the chondropathies as targets of treatment according to the present invention include, but are not limited to, osteoarthritis, cartilage injury and chondrodysplasia. The chondropathies as the most preferred targets to which treatment according to the present invention is to be applied are diseases associated with dyschondroplasia during the growth of the cartilage. Such diseases are not particularly limited as long as they have the above clinical conditions, but examples of the diseases include those with mutations in FGFR (FGFR1, FGFR2 or FGFR3). Specific examples of the diseases include those described in Warman et al., Am J Med Genet 155A(5): 943-68 (2011). Preferably, the therapeutic agent identified by the present invention is applied to FGFR3 diseases.

A preferred therapeutic and/or prophylactic agent of the present invention for diseases with FGFR mutations (e.g., FGFR3 diseases) is a medicament comprising a HMG-CoA reductase inhibitor. Examples of the HMG-CoA reductase inhibitor in the present invention include, but are not limited to, mevastatin (compactin) (see U.S. Pat. No. 3,983,140), pravastatin (see JP S57-2240 A (U.S. Pat. No. 4,346,227)), lovastatin (see JP S57-163374 A (U.S. Pat. No. 4,231,938)), simvastatin (see JP S56-122375 A (U.S. Pat. No. 4,444,784)), fluvastatin (see JP S60-500015 A (U.S. Pat. No. 4,739,073)), atorvastatin (see JP H3-58967A (U.S. Pat. No. 5,273,995)), rosuvastatin (see JP H5-178841 A (U.S. Pat. No. 5,260,440)), and pitavastatin (see JP H1-279866 A (U.S. Pat. No. 5,854,259 and U.S. Pat. No. 5,856,336)). Preferred HMG-CoA reductase inhibitors in the present invention are drugs selected from the group consisting of mevastatin, atorvastatin, pravastatin, rosuvastatin, fluvastatin and lovastatin.

The HMG-CoA reductase inhibitors used in the present invention, i.e., mevastatin, pravastatin, lovastatin, simvastatin, fluvastatin, atorvastatin, rosuvastatin and pitavastatin include their closed lactone ring forms or their pharmaceutically acceptable salts (preferably, sodium salts, calcium salts, etc.).

The substance identified by the screening method of the present invention can be formulated by a conventional method into a therapeutic and/or prophylactic agent for FGFR3 diseases. For example, the substance may be formulated into a composition for oral administration in a solid or liquid dosage form. Specific examples of the oral composition include tablets (such as sugar-coated tablets and film-coated tablets), pills, granules, powders, capsules (such as soft capsules), syrups, emulsions, and suspensions. The substance may be formulated into a composition for parenteral administration, such as injections and suppositories. Examples of the injections may include injection forms such as intravenous injections, subcutaneous injections, intradermal injections, intramuscular injections, and intravenous drips. These formulations are produced by a conventional method using additives, including excipients (e.g., organic excipients, including sugar derivatives such as lactose, sucrose, glucose, mannitol and sorbitol; starch derivatives such as corn starch, potato starch, pregelatinized starch and dextrin; cellulose derivatives such as crystalline cellulose; gum arabic; dextran; pullulan; and inorganic excipients, including silicate derivatives such as light anhydrous silicic acid, synthetic aluminum silicate, calcium silicate, and magnesium aluminometasilicate; phosphates such as calcium hydrogen phosphate; carbonates such as calcium carbonate; and sulfates such as calcium sulfate); lubricants (e.g., stearic acid; metal stearates such as calcium stearate and magnesium stearate; talc; colloidal silica; waxes such as beeswax and whale wax; boric acid; adipic acid; sulfates such as sodium sulfate; glycol; fumaric acid; sodium benzoate; DL-leucine; lauryl sulfates such as sodium lauryl sulfate and magnesium lauryl sulfate; silicic acids such as silicic anhydride and silicic acid hydrate; and starch derivatives as described above); binders (e.g., hydroxypropyl cellulose, hydroxypropyl methylcellulose, polyvinylpyrrolidone, macrogol, and excipients as described above); disintegrants (e.g., cellulose derivatives such as low-substituted hydroxypropyl cellulose, carboxymethyl cellulose, carboxymethyl cellulose calcium, and internally cross-linked carboxymethylcellulose sodium; and chemically modified starches and celluloses, such as carboxymethyl starch, carboxymethyl starch sodium, and cross-linked polyvinylpyrrolidone); emulsifiers (e.g., colloidal clays such as bentonite and Veegum; metal hydroxides such as magnesium hydroxide and aluminum hydroxide; anionic surfactants such as sodium lauryl sulfate and calcium stearate; cationic surfactants such as benzalkonium chloride; and nonionic surfactants such as polyoxyethylene alkyl ether, polyoxyethylene sorbitan fatty acid ester, and sucrose fatty acid ester); stabilizers (p-hydroxybenzoic acid esters such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid); flavors and odor improvers (e.g., commonly used sweeteners, acidulants, and fragrances); and diluents.

The dosage of the drug of the present invention to a patient varies with the type of disease to be treated, the severity of the symptom and the disease, the age, sex and body weight of the patient, the route of administration, etc. The dosage is thus cannot be definitely specified, but an adequate dosage can be determined as appropriate by a physician in consideration of the above conditions.

A single oral dose of, for example, from 0.1 mg (preferably 0.5 mg) to 1000 mg (preferably 500 mg) or a single parenteral dose of, for example, from 0.01 mg (preferably 0.05 mg) to 100 mg (preferably 50 mg) can be administered to an adult once to six times a day. The dose may be increased or reduced depending on the symptom.

EXAMPLES

The present invention will be specifically described with reference to Examples below, but the scope of the present invention is not limited to the Examples.

Example 1

Generation of iPS Cells

All experiments described below were approved by the institutional review board, the institutional animal committee, the institutional biosafety committee, and Kyoto University.

HDFs derived from three TD patients (TD-714, TD10749, and TD-315H) were obtained from Coriell Institute for Medical Research and Saitama Children's Medical Center. A sequencing analysis of the genomic cDNAs extracted from the HDFs revealed a heterozygous mutation (Arg248Cys) in the FGFR3 gene in all three TD patients. iPS cell lines were generated from the HDFs of the patients as described below (hereinafter called TD-iPSCs), and one iPS cell line derived from each patient (TD-714-3, TD10749-2 and TD315H-2) was analyzed. Control HDFs from two different neonates were purchased from KURABO (strains #01491 and #01439), and reprogrammed in the same manner as in the generation of TD-iPSCs to generate control iPS cells (KF4009-1 and HDF-11). Another iPS cell line derived from an healthy individual (409B2) (Okita, K., et al. Nature methods 8, 409-412 (2011)) gifted from K. Okita and S. Yamanaka (Center for iPS Cell Research and Application (CiRA), Kyoto University) was also used as control iPS cells (hereinafter KF4009-1, HDF-11 and 409B2 are collectively called WT-iPSCs).

The iPS cells were generated as follows. Briefly, the human fibroblasts (HDFs) were cultured in DMEM (Sigma) supplemented with 10% FBS (Invitrogen), 50 U/ml penicillin and 50 µg/ml streptomycin. Episomal plasmid vectors (Mixture Y4: OCT3/4, SOX2, KLF4, L-MYC, LIN28 and p53 shRNA) were electroporated into the HDFs using Neon Transfection System (Invitrogen) (Okita, K., et al. Nature methods 8, 409-412 (2011)). One week after transduction, $1 \times 10^5$ HDFs carrying the vectors were seeded into 100 mm dishes pre-seeded with feeder cells. The cells were then cultured in hiPSC medium (DMEM/F12 (Sigma) supplemented with 20% KSR (Invitrogen), 2 mM L-glutamine (Invitrogen), $1 \times 10^{-4}$ M nonessential amino acids (Invitrogen), $1 \times 10^{-4}$ M 2-mercaptoethanol (Invitrogen), 50 units/ml penicillin (Invitrogen), 50 µg/ml streptomycin (Invitrogen) and 4 ng/ml bFGF(WAKO)). The obtained iPS cell lines were analyzed by immunohistochemistry using an anti-SSEA4 antibody (Santa Cruz, sc-5279) and an anti-TRA1-60 antibody (Abcam, ab16287).

Figure 1B:
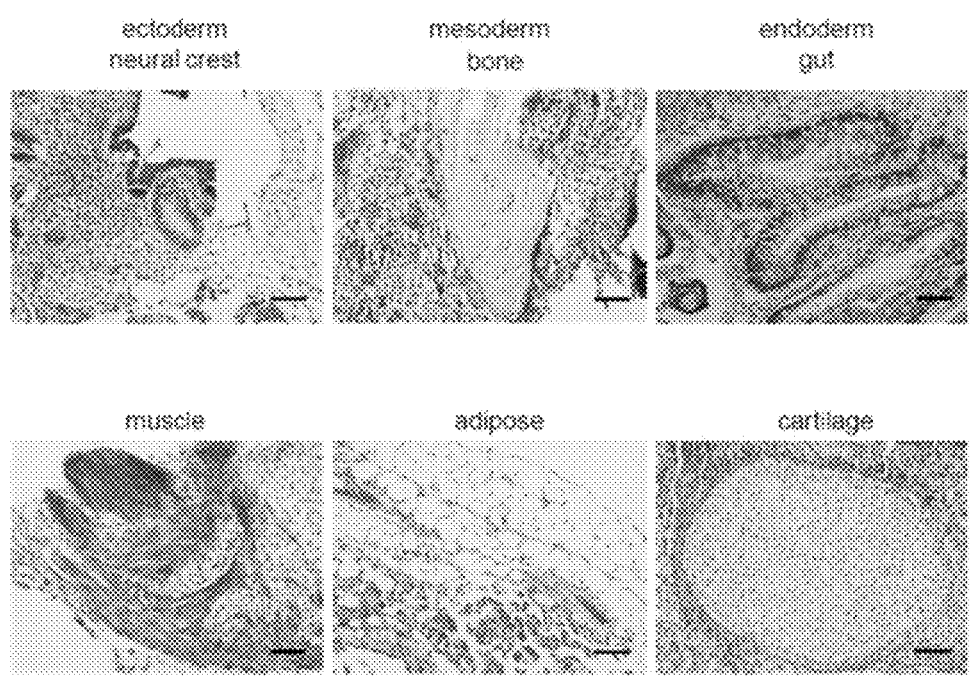

The analysis confirmed that all the generated iPSC lines expressed ES cell markers (SSEA4 and TRA1-60) and formed teratomas containing all three germ layers (FIGS. 1A and 1B and Table 1).

TABLE 1

| iPSC line | Sex | Age at sampling | Race | ID (cell bank)/lot (company) | Origin | FGFR3 mutations | iPSCs Expression of ES cell markers | iPSCs Formation of teratomas |
|---|---|---|---|---|---|---|---|---|
| TD714-3 | M | 1 d | Caucasian | GM00714 (Coriell) | Fibroblast | 742C > T [Arg248Cys] | Yes | Yes |
| TD10749-2 | M | 1 d | Caucasian | GM10749 (Coriell) | Fibroblast | 742C > T [Arg248Cys] | Yes | Yes |
| TD315H-2 | F | 21 weeks and 4 days gestation | Japanese | S2012 (Saitama) | Fibroblast | 742C > T [Arg248Cys] | Yes | Yes |
| 409B2 | F | 36 y | | | Fibroblast | No | Yes | Yes |
| KF4009-1 | M | Newborn | Asian/ Caucasian | 01491 (Kurabo) | Fibroblast | No | Yes | Yes |
| HDF-11 | M | Newborn | Asian | 01439 (Kurabo) | Fibroblast | No | Yes | Yes |

Determination of mRNA mRNAs were isolated from the cell lines using RNeasy Mini Kit (Qiagen). A total of 500 ng of the total RNA was used as a template for cDNA synthesis by reverse transcription using ReverTra Ace system (TOYOBO). Standard curves for quantitative PCR (real-time PCR) were established and used for analyses. Real-time PCR analysis was performed in Step One system (ABI) using KAPA SYBR FAST qPCR kit Master Mix ABI Prism (KAPA BIOSYSTEMS). The sequences and Assay IDs of the primers used are shown in Table 2.

TABLE 2

| Primer | Sequence or Assay ID | SEQ ID NO |
|---|---|---|
| β-ACTIN F | TGGCACCACACCTTCTACAATGAGC | 1 |
| β-ACTIN R | GCACAGCTTCTCCTTAATGTCACGC | 2 |
| SOX9 F | AGACCTTTGGGCTGCCTTAT | 3 |
| SOX9 R | TAGCCTCCCTCACTCCAAGA | 4 |
| AGGRECAN F | TGAGGAGGGCTGGAGACAAGTA | 5 |
| AGGRECAN R | GGAGGTGGTAATTGCAGGGAACA | 6 |
| COL2A1 F | TTTCCCAGGTCAAGATGGGTC | 7 |
| COL2A1 R | CTTCAGCACCTGTCTCACCA | 8 |
| COL1A1 F | GTCGAGGGCCAAGACGAAG | 9 |
| COL1A1 R | CAGATCACGTCATCGCACAAC | 10 |
| COL1A2 F | AATTGGAGCTGTTGGTAACGC | 11 |
| COL1A2 R | CACCAGTAAGGCCGTTTGC | 12 |
| Taqman β-ACTIN | Hs 01060665.g1 | – |
| Taiwan FGFR3 | Hs 00179829-m1 | – |

Western Blotting

Cell lysates were separated by SDS-PAGE. The separated proteins were immunostained with anti-FGFR3 antibody (Cell Signaling, #4574), anti-phosphorylated MAPK antibody (Cell Signaling, #9109) or anti-β-actin antibody (Cell Signaling, #49776).

Example 2

Induction of Cartilage

The iPS cell lines were induced to differentiate into chondrocytes following the previously described method (Oldershaw, R. A., et al., Nat Biotechnol 28, 1187-1194 (2010)) with modifications, as described below.

The iPS cell lines were transferred to Matrigel (Invitrogen)-coated dishes, then Essential 8 medium (Life Technologies) supplemented with 50 units/ml penicillin and 50 μg/ml streptomycin was added, and the cell lines were cultured for undifferentiated maintenance under the feeder-free conditions. The iPS cell lines formed colonies that consisted of 1 to 2×10$^5$ cells 10 to 15 days after seeding, and the medium was changed to mesodermal differentiation medium (DMEM/F12 supplemented with 10 ng/ml Wnt3A (R&D), 10 ng/ml activin A (R&D), 1% insulin-transferrin-sodium selenite (Invitrogen), 1% fetal calf serum, 50 units/ml penicillin and 50 μg/ml streptomycin) (day zero of differentiation). Three days after (day 3 of differentiation), the medium was changed to cartilage differentiation medium (DMEM/F12 supplemented with 50 μg/ml ascorbic acid, 10 ng/ml BMP2 (Osteopharma), 10 ng/ml TGFβ (PeproTech), 10 ng/ml GDF5, 1% insulin-transferrin-sodium selenite, 1% FBS, 50 units/ml penicillin and 50 μg/ml streptomycin). Eleven days after (day 14 of differentiation), the cells were physically separated from the dishes, and transferred to a suspension culture in the same medium. Fourteen days after transfer (day 28 of differentiation) and 28 days after transfer (day 42 of differentiation), the cells formed particles and the particles were harvested for analyses. The culture medium was changed every 2 to 7 days during differentiation.

WT-iPSCs formed particles composed of cells scattered in cartilaginous extracellular matrix, as indicated by positive safranin O staining on day 42 of differentiation, whereas TD-iPSCs formed particles that did not contain cartilaginous extracellular matrix (FIGS. 2A and 2B). The results indicate that the TD-iPSC-derived particles contained little glycosaminoglycan, which is important for cartilage structure.

Figure 3A:
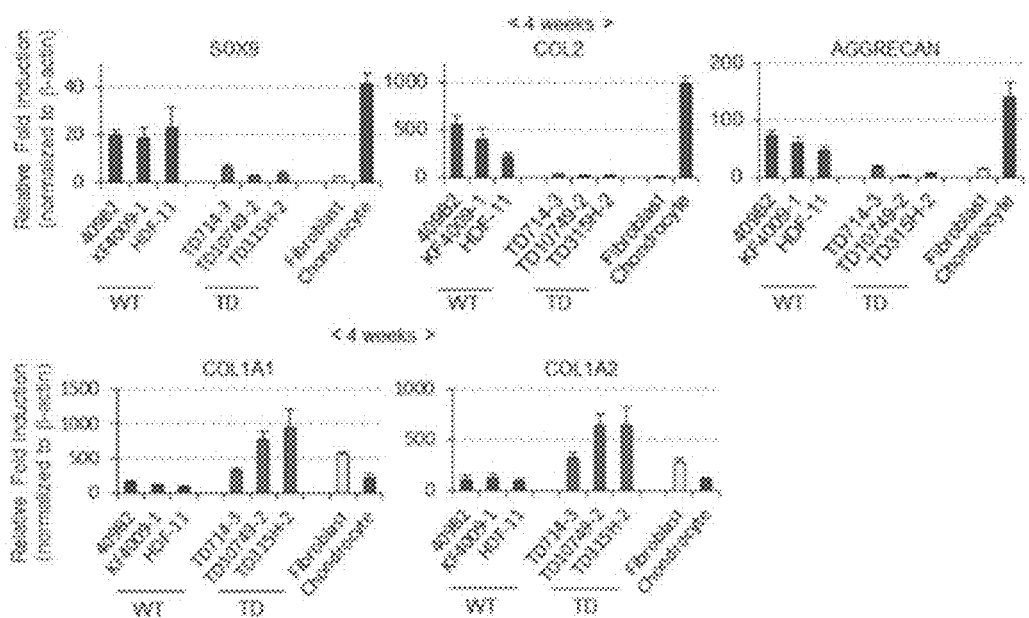
FIGS. 3A to 3C show the results of analysis of the chondrocytes differentiated from TD-iPSCs and WT-iPSCs.

FGFR3 mRNA expression levels were measured. Expression analysis of chondrocyte marker genes (SOX9, COL2 and AGGRECAN) and type I collagen genes on day 28 of differentiation showed that there were decreased expression levels of the chondrocyte markers and increased expression levels of the type I collagen genes in the TD-iPSC-derived cells (FIG. 3A).

Figure 3B:
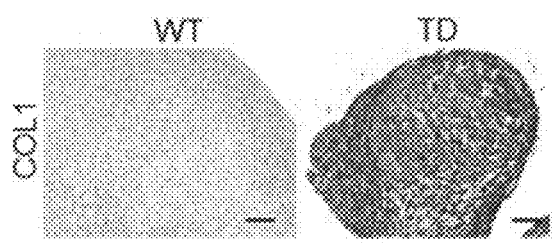
Figure 3C:
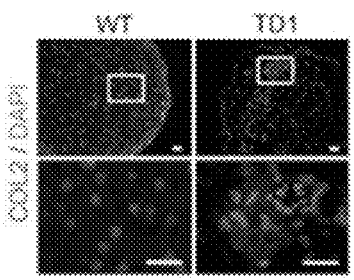

Immunohistochemical analysis on day 42 of differentiation showed that the TD-iPSC-derived particles expressed less type II collagen and more type I collagen than the WT-iPSC-derived particles (FIG. 3B). The immunohistochemical analysis was performed as follows. The particles were collected on day 42 of differentiation, fixed with 4% paraformaldehyde, processed and embedded in paraffin, and semi-serial sections were prepared. Type I collagen was detected with anti-type I collagen antibody (SouthernBiotech, 1320-01). DAB (DAKO, K3468) was used as a chromogen. Focal deposition of type II collagen in the TD-iPSC-derived particles (FIG. 3C) suggests that there was limited cartilage formation or remnant cartilage that was formed in earlier stages and was subsequently degraded.

Figures 4A, 4B, 4C:
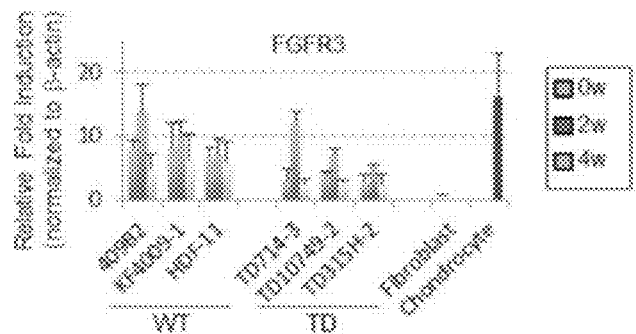
FIGS. 4A to 4D show the results of analysis of the chondrocytes differentiated from TD-iPSCs and WT-iPSCs.

The expression level of FGFR3 mRNA in the differentiated TD-iPSCs (week zero, week 2 (day 14) and week 4 (day 28)) was lower than in the differentiated WT-iPSCs (FIGS. 4A and 4B), probably because of the negative feedback regulation due to hyperactivity induced by FGFR3 mutations in the TD cells. Analysis of the amount of FGFR3 protein showed that the protein in the TD-iPSC-derived chondrocytes was higher than in the WT-iPSC-derived chondrocytes (FIG. 4C), supporting the notion that the mutant FGFR3 receptor is resistant to degradation, leading to persistent activation of the receptor's signal transduction.

Figure 4D:
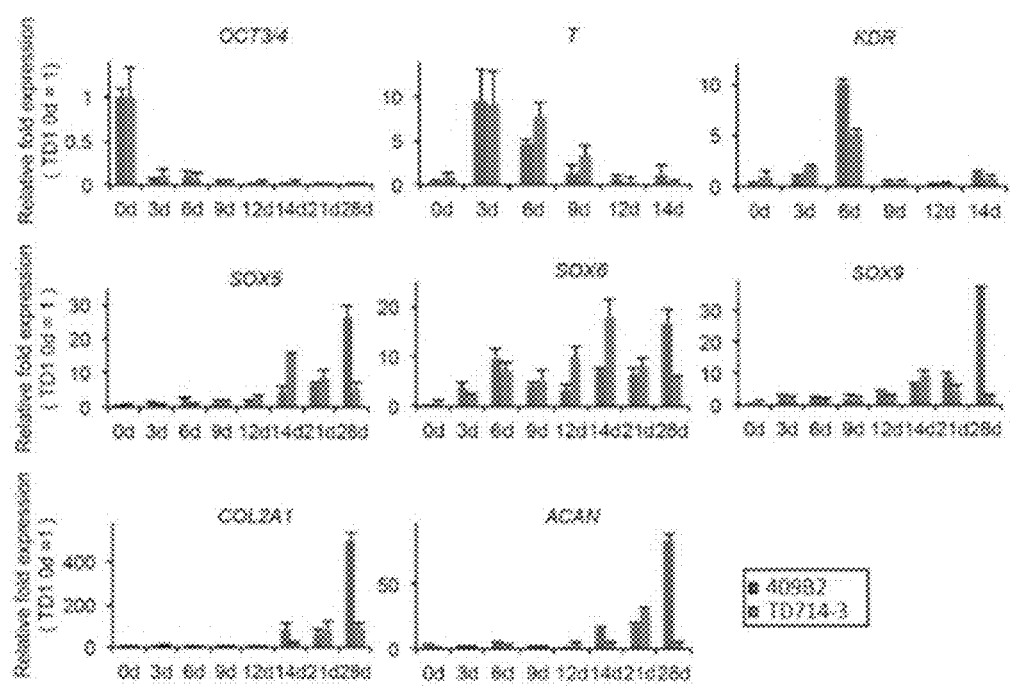

To examine how the chondrogenic differentiation of TD-iPSCs resulted in the formation of abnormal particles, the time course of the changes in the expression of markers was analyzed in WT-iPSCs and TD-iPSCs subjected to chondrogenic differentiation (FIG. 4D). Expression of OCT3/4, a marker of pluripotency, decreased rapidly on day 3, and expression of mesendodermal/mesodermal markers T and KDR was transiently increased on days 3 to 9 in both WT-iPSCs and TD-iPSCs. Expression of chondrogenic transcription factors SOX9, SOX5 and SOX6 was also increased in both WT-iPSCs and TD-iPSCs until day 14. After day 14, expression levels of the chondrogenic transcription factors continued to increase in WT-iPSCs, whereas they decreased in TD-iPSCs.

These chondrogenic transcription factors are related to the transcription of genes encoding cartilage matrix proteins. Expression analysis of type II collagen gene (COL2A1) and aggrecan gene (ACAN) showed a gradual increase in both WT-iPSCs and TD-iPSCs until day 21. The expression levels of COL2A1 and ACAN continued to increase in WT-iPSCs, whereas they were decreased on day 28 in TD-iPSCs. These findings suggest that WT-iPSCs and TD-iPSCs showed similar differentiation ability until days 14 to 21. Reduced expression of the cartilage matrix genes on day 28, however, indicated that chondrocyte maturation was disturbed in TD-iPSCs.

Figure 5A:
FIGS. 5A to 5F show the results of analysis of the chondrocytes differentiated from TD-iPSCs and WT-iPSCs.
Figure 5B:
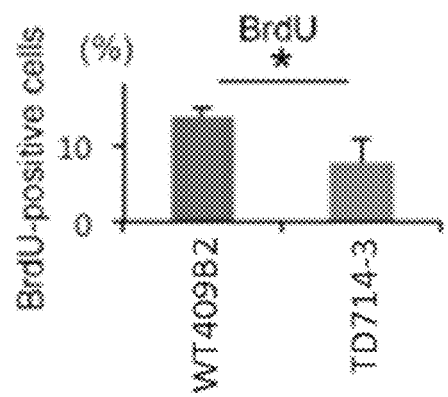
Figure 5C:
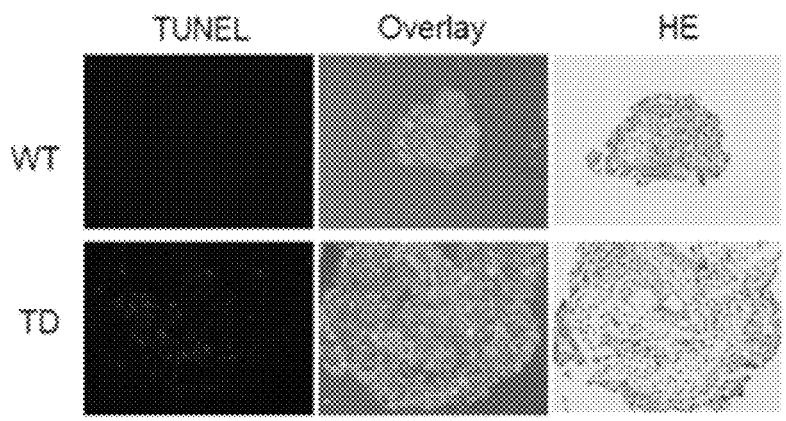
Figure 5D:
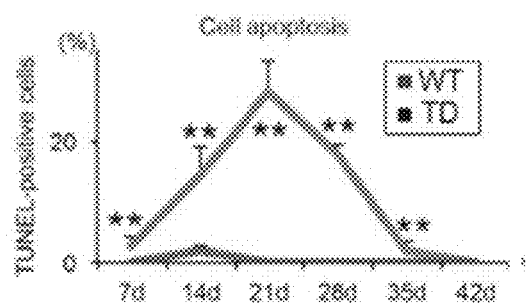
Figure 5E:
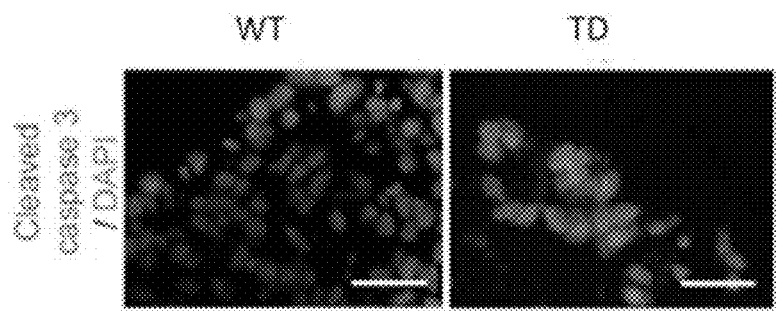
Figure 5F:
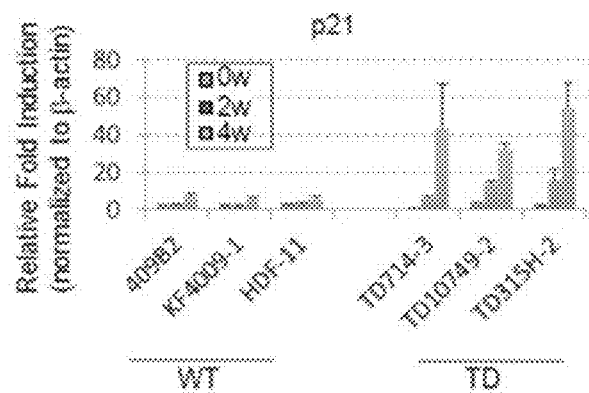

Labelling cells with BrdU for the determination of the proliferation rates of the TD-iPSC and WT-iPSC-derived chondrocytes revealed that the proliferation rate of the TD-iPSC-derived chondrocytes was significantly decreased compared with that of the WT-iPSC-derived chondrocytes on day 28 (FIGS. 5A and 5B). TUNEL assay of the TD-iPSC-derived cartilaginous particles showed increased numbers of TUNEL-positive cells, i.e., cells undergoing apoptosis, on day 21 of differentiation (FIGS. 5C and 5D) and an increased number of cleaved-caspase 3-positive cells (FIG. 5E), suggesting that the TD-iPSC-derived chondrocytes had increased apoptosis. The TD-iPSC-derived chondrocytes also showed increased expression levels of p21 (FIG. 5F). Taken together, these results suggest that the chondrogenically differentiated TD-iPSCs recapitulates the two abnormalities that are found in FGFR3 disease patients and models: decreased cell proliferation and increased apoptosis. These two abnormalities might be responsible for the cartilage defects found in the TD-iPSC-derived cartilaginous particles on day 42. For the TUNEL assay, In Situ Cell Death Detection Kit (TMR red; Roche) was used according to the manufacturer's instructions.

Example 3

Recovery from Disturbed Cartilage Formation in Chondrogenically Differentiated TD-iPSCs To confirm that TD-iPSCs cause failure of chondrogenic differentiation due to the gain-of-function mutation of FGFR3, FGFR3 knock-down experiments were performed.

Figure 6A:
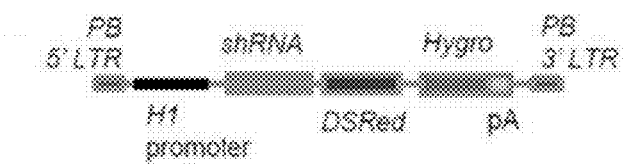
FIGS. 6A to 6E show the results of analysis of chondrogenically differentiated TD-iPSCs (TD714-3) transduced with FGFR3 shRNAs.

A shRNA PB vector and a transposase expression vector (PBaseII, P16-25) were a gift from A. Hotta (Center for iPS Cell Research and Application (CiRA), Kyoto University, Kyoto, Japan). PiggyBac vectors carrying three short hairpin RNAs (shRNAs) targeting different sites of FGFR3 (FGFR3 shRNA PB vectors) were generated based on the shRNA PB vector (FIG. 6A). The sequences for generating shRNA constructs are shown in Table 3.

The FGFR3 shRNA PB vectors and PBaseII were introduced into TD-iPSCs (TD714-3) using Nucleofection (Amaxa) according to the manufacturer's instructions to knock-down FGFR3 in TD-iPSCs. The TD-iPSCs were chondrogenically differentiated in the same manner as in Example 2, and the cartilaginous particles were assessed on days 28 and 42 of differentiation. RNA expression analysis was carried out in the same manner as in Example 1.

Figure 6B:
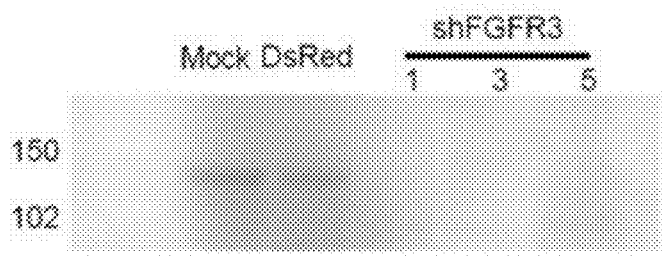
Figure 6C:
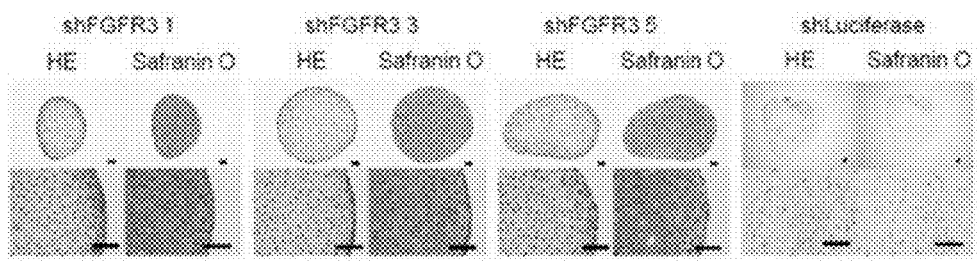
Figure 6D:
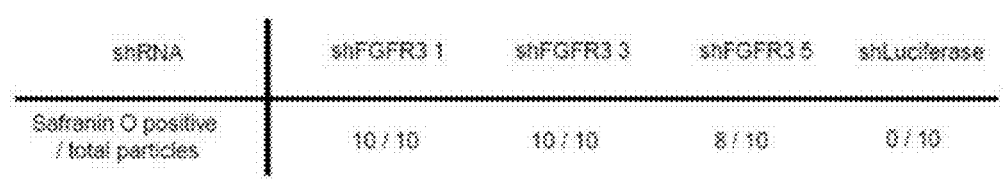
Figure 6E:
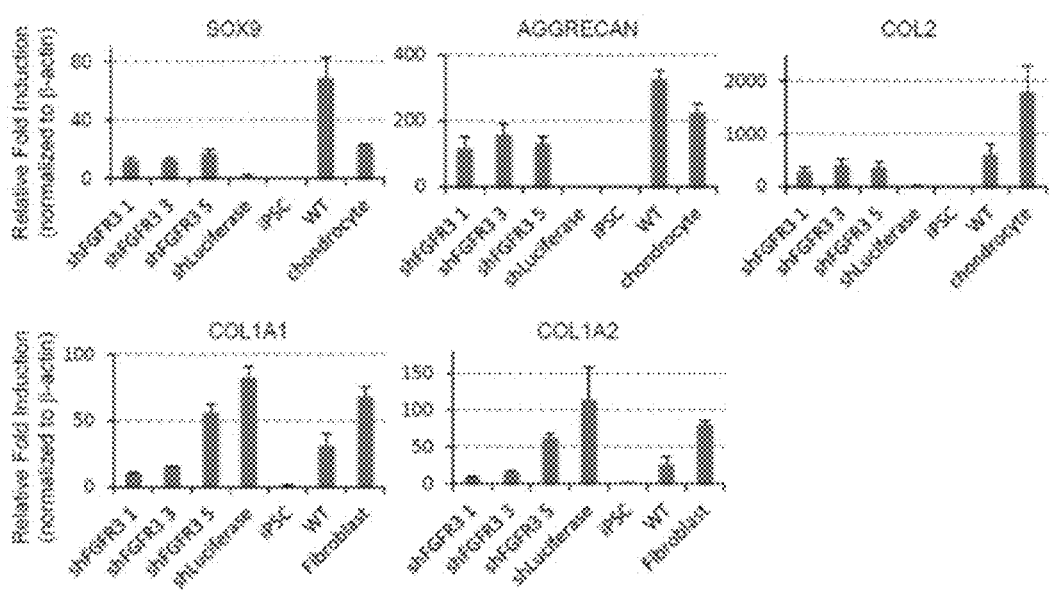

Expression of the FGFR3 gene was knocked down by three types of FGFR3 shRNA PB vectors (FIG. 6B). TD-iPSCs with knocked-down expression of FGFR3 by the FGFR3 shRNA PB vectors formed particles containing cartilaginous extracellular matrix (FIGS. 6C and 6D). Gene expression analysis showed that the TD-iPSC-derived particles transduced with FGFR3 shRNA had increased expression of chondrocyte marker genes and decreased expression of fibroblast marker genes (COL1A1 and COL1A2) compared with the TD-iPSC-derived particles transduced with a negative control shLuciferase (shRNA targeting the luciferase gene sequence) (FIG. 6E).

FGFR3 neutralizing antibody was added to the medium during the chondrogenic differentiation of TD-iPSCs to inhibit FGFR3 activity, and chondrocyte formation was assessed. The FGFR3 neutralizing antibody (Santa Cruz (sc-13121)) was added as 1 µl of an antibody solution (200 ng/ml) in 1 ml of cartilage differentiation medium. As a control, IgG (Cell Signaling, #27295) was used. The chondrogenic differentiation was performed in the same manner as in Example 2, and the cartilaginous particles were assessed on days 28 and 42 of differentiation.

Addition of the FGFR3 neutralizing antibody resulted in the formation of cartilaginous extracellular matrix in particles, similarly to that observed in FGFR3 gene knock-down (FIGS. 7A and 7B). Gene expression analysis showed that addition of the FGFR3 neutralizing antibody increased the expression of chondrocyte marker genes and decreased the expression of fibroblast marker genes (FIG. 7C).

These results suggest that failure of chondrogenic differentiation of TD-iPSCs is caused by the gain-of-function mutations of FGFR3.

TABLE 3

| Primer | Sequence | SEQ ID NO |
|---|---|---|
| shFGFR3-1 F | GATCCTACACCTGCGTCGTGGAGAACAAGTTTGTGAAGC AGATGAAACTTGTTCTCCACGACGCAGGTGTATTTTTG | 13 |
| shFGFR3-1 R | AATTCAAAAATACACCTGCGTCGTGGAGAACAAGTTTCAT CTGCTTCACAAACTTGTTCTCCACGACGCAGGTGTAG | 14 |
| shFGFR3-3 F | GATCCGATGCTGAAAGACGATGCCACTGACAACATCTGC TTCACTTGTCATGGCATCGTCTTTCAGCATCTTTTTG | 15 |
| shFGFR3-3 R | AATTCAAAAAGATGCTGAAAGACGATGCCACTGACAAGT GAAGCAGATGTTGTCAGTGGCATCGTCTTTCAGCATCG | 16 |
| shFGFR3-5 F | GATCCCTGCACACACGACCTGTACATGATCATCATGTGCT TCACATGATCATGTACAGGTCGTGTGTGCAGTTTTTG | 17 |
| shFGFR3-5 R | AATTCAAAAACTGCACACACGACCTGTACATGATCATGTG AAGCAGATGATGATCATGTACAGGTCGTGTGTGCAGG | 18 |
| shLuciferase F | GATCCGTGCGTTGTTAGTACTAATCCTATTTGTGAAGA GATGAAATAGGGTTGGTACTAGCAACGCACTTTTTG | 19 |
| shLuciferase R | AATTCAAAAAGTGCGTTGCTAGTACCAACCCTATTTCATC TGCTTCACAAATAGGATTAGTACTAACAACGCACG | 20 |

Example 4

Evaluation of Known Drugs for their Ability to Rescue TD-iPSCs from Failure of Chondrogenic Differentiation To find effective drugs to treat FGFR3 diseases, screening of substances for their ability to rescue TD-iPSCs from failure of chondrogenic differentiation was performed.

Several drugs that had previously been reported to affect FGFR3 signaling and/or chondrocyte differentiation (CNP, NF449, a FGFR inhibitor, and an IGF1R inhibitor) were selected, and their ability to rescue TD-iPSCs from failure of chondrogenic differentiation was investigated. The stock CNP (Sigma, N8768), NF449 (Abcam, ab120415), a FGFR inhibitor (PD 173047, Cayman) and an IGF1R inhibitor (IGF-1R inhibitor, PPP. Calbiochem, 407247) solutions were prepared at a concentration of 100 µM, 50 mM, 1 mM, 1 µM, respectively. The stock solutions were added to cartilage differentiation medium at the final concentrations of CNP, NF449, the FGFR inhibitor and the IGF1R inhibitor of 100 nM, 25 µM 1 µM, and 1 nM, respectively (day 3 of differentiation). TD-iPSCs were chondrogenically differentiated in the same manner as in Example 2, and the cartilaginous particles were assessed on days 28 and 42 of differentiation. As a control, an equal volume of water or DMSO was added to the medium. mRNA expression analysis was performed in the same manner as in Example 1.

The addition of the FGFR inhibitor or the G-protein antagonist NF449 had no effect on the chondrogenic differentiation of TD-iPSCs, but the addition of the IGF1R inhibitor and CNP rescued TD-iPSCs from failure of chondrogenic differentiation (FIGS. 8A and 8B). Gene expression analysis showed that addition of the IGF1R inhibitor or CNP increased the expression of chondrocyte marker genes and decreased the expression of fibroblast marker genes (FIG. 8C).

Example 5

Search for Drugs for Rescuing TD-iPSCs from Failure of Chondrogenic Differentiation Statins compose a drug class broadly characterized as lipid-lowering agents. Statins inhibit mevalonic acid synthesis, and as a consequence lead to a decrease in the amount of total cholesterol and decreased levels of low-density lipoproteins (LDLs). Statins have favorable effects on cardiovascular diseases, the nervous system, the immune system, the skeletal system and tumor growth, and there is emerging interest in the pleiotropic effects of statins. Lovastatin is reported to inhibit the loss of the type II collagen that occurs due to dedifferentiation caused by monolayer culture of the cells isolated from the nucleus pulposus (Hu et al., Artif Organs. 35, 411-416, 2011).

To investigate whether lovastatin rescues TD-iPSCs from failure of chondrogenic differentiation, evaluation was performed in the same manner as in Example 4. A stock lovastatin (TCI, L0214) solution was prepared by dissolving it in DMSO at a concentration of 10 mM, and the solution was added to cartilage differentiation medium at a final concentration of 1 µM.

Figure 10A:
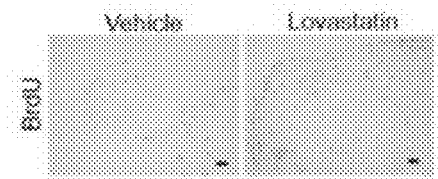
FIGS. 10A to 10E show the results of chondrogenic induction from TD-iPSCs in the presence of statins.
Figure 10B:
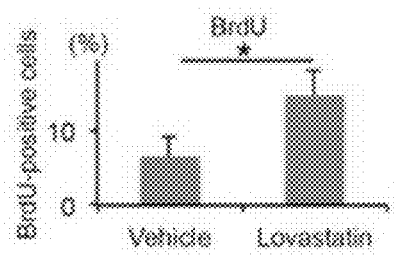
Figure 10C:
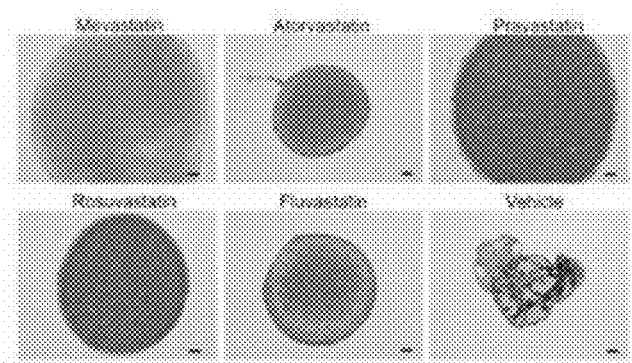
Figure 10D:
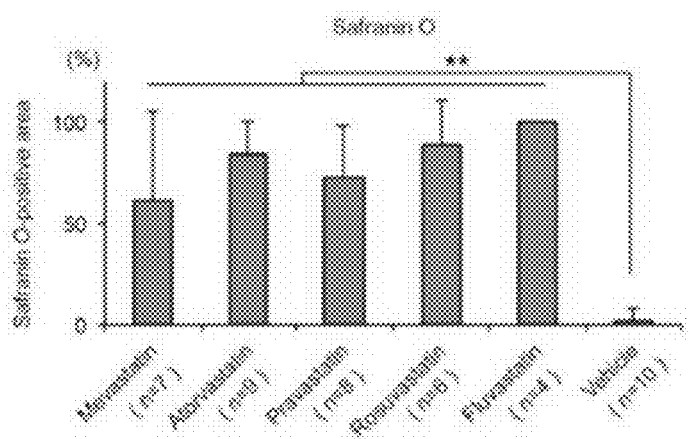

The addition of lovastatin rescued the chondrogenic differentiation of TD-iPSCs (FIGS. 9A and 9B). Gene expression analysis showed that the addition of lovastatin increased the expression of chondrocyte marker genes and decreased the expression of fibroblast marker genes (FIG. 9C). Incorporation of BrdU by the TD-iPSC-derived cartilaginous particles cultured in the presence or absence of rosuvastatin revealed that the addition of rosuvastatin significantly increased the number of BrdU-positive cells (FIGS. 10A and 10B). The addition of mevastatin (Cayman, 10010340), atorvastatin (LKT A7658), pravastatin (Cayman, 10010343), rosuvastatin (BioVision, 1995-5), or fluvastatin (Cayman, 10010337) was also investigated in the same manner as above, and these drugs also rescued abnormal cartilage formation in the TD-iPSC-derived chondrocytes (FIGS. 10C and 10D). These statins were prepared as a 10 mM DMSO solution, and added as appropriate to the medium at a final concentration of 1 µM. These results suggest that various statins can rescue TD-iPSC-derived chondrocytes.

Figure 10E:
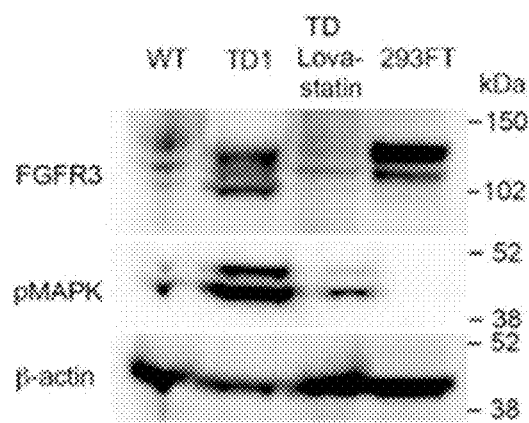
Figure 10F:
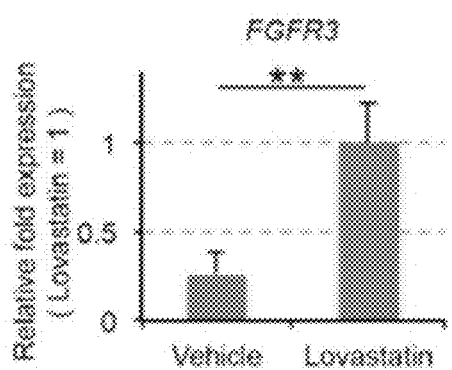
FIG. 10F shows the results of quantitative PCR analysis of the expression level of FGFR3 in TD-iPSCs chondrogenically differentiated with or without lovastatin on day 28.

To investigate the mechanism(s) by which statins rescue FGFR3 diseases, the expression levels of FGFR3 mRNA and protein were determined. The analysis revealed that addition of lovastatin reduced an abnormally increased amount of FGFR3 protein in the TD-iPSC-derived chondrocytes (FIG. 10E). Addition of lovastatin also reduced phosphorylated MAPK, a downstream target of FGFR3 signaling. Since the FGFR3 mRNA expression levels were increased by addition of lovastatin in the TD-iPSC-derived chondrocytes, the changes in the amount of FGFR3 protein were not regulated at the mRNA expression level (FIG. 10F).

Example 6

Effects of Lovastatin on ACH

To investigate whether lovastatin is also effective for ACH, iPS cells were generated from ACH patients and evaluations were performed in the same manner as above.

HDFs from two patients with ACH who had a heterozygous mutation (Gly380Arg) in the FGFR3 gene (ACH8857 and ACH8858) and HDFs from one patient who had more serious dyschondroplasia than the ACH (ACHhomo-8859) were obtained from Coriell Institute for Medical Research. ACH patient-derived iPS cells were generated from these HDFs in the same manner as in Example 1. ACHhomo-8859 had a homozygous mutation (Gly380Arg) in the FGFR3 gene. One type of iPSC line was generated from each patient (iPSC lines ACH8857-1, ACH8858-6, and ACHhomo8859-3 were generated) (hereinafter, ACH8857-1 and ACH8858-6 are collectively called ACH-iPSCs, and ACHhomo8859-3 is called ACHhomo-iPSCs). ACH-iPSCs and ACHhomo-iPSCs expressed SSEA4 and TRA1-60, and formed teratomas containing all three germ layers (Table 4).

TABLE 4

| iPSC line | Sex | Age at sampling | Race | ID (cell bank)/lot (company) | Origin | FGFR3 mutations | iPSCs Expression of ES cell markers | Formation of teratomas |
|---|---|---|---|---|---|---|---|---|
| ACH8857-1 | M | 34 y | Caucasian | GM08857 (Coriell) | Fibroblast | 1138G > A [Gly380Arg] | Yes | Yes |
| ACH8858-6 | F | 30 y | Caucasian | GM08858 (Coriell) | Fibroblast | 1138G > A [Gly380Arg] | Yes | Yes |
| ACHhomo 8859-3 | F | 1 m | Caucasian | GM08859 (Coriell) | Fibroblast | 1138G > A [Gly380Arg] homozygous | Yes | Yes |

Figures 11A, 11B:
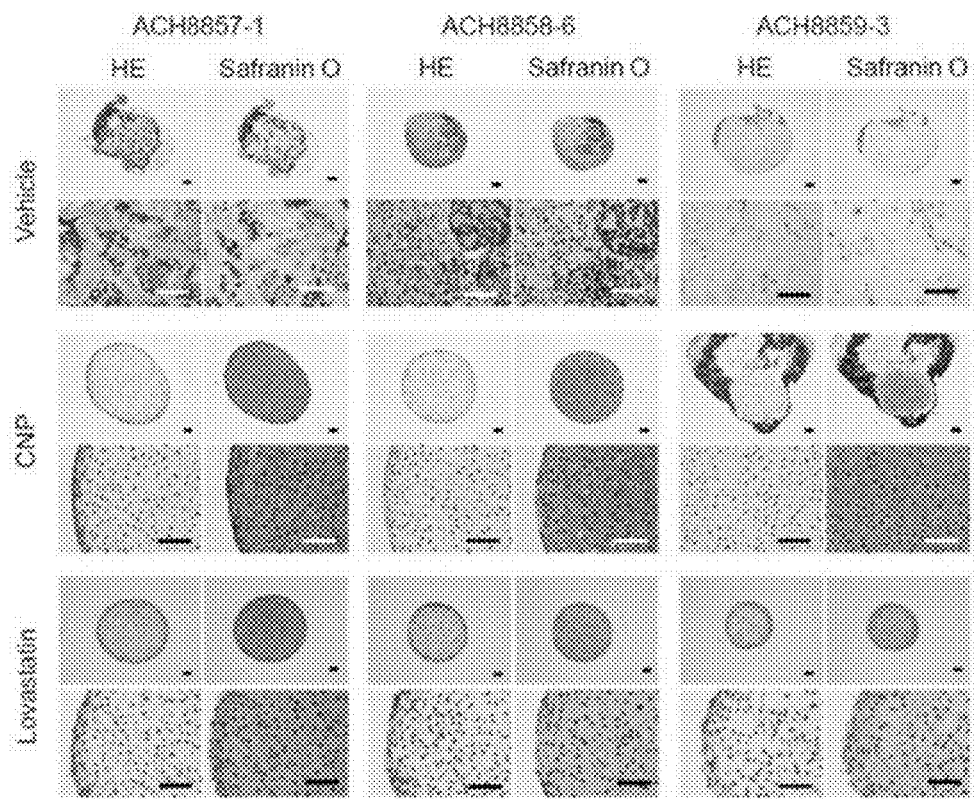
FIGS. 11A and 11B show the results of chondrogenic induction from ACH-iPSCs in the presence of lovastatin or CNP.

The chondrogenic differentiation of ACH-iPSCs and ACHhomo-iPSCs in the same manner as in Example 2 resulted in the formation of particles that were negative for safranin O staining (FIG. 11A). Addition of lovastatin in the same manner as in Example 5 rescued the cartilage formation of chondrogenically differentiated ACH-iPSCs and partially rescued the cartilage formation of ACHhomo-iPSCs (FIG. 11B).

Taken together, these results suggest that lovastatin rescues the cartilage formation in the TD-iPSC and ACH-iPSC models.

Example 7

Statins rescue ACH model mice from reduced bone growth Whether statins rescue the FGFR3 disease phenotype in vivo was examined. FGFR3$^{ACh}$ mice (Naski et al., Development 125, 4977-4988 (1998)) were a gift from David Ornitz (Washington University School of Medicine). The FGFR3$^{Ach}$ mice were crossed with wild-type mice (C57BL/6 background). A rosuvastatin solution at a dose of 1.0 mg/kg was intraperitoneally administered to the crossed mice 6 times per week from 3 days after birth until day 14. The mice were euthanized on day 15, and the bodies and the bone formation were examined by X-ray imaging (Faxitron DX-50). Genomic DNA was extracted from the toes of each mouse and subjected to genotype analysis. Also, a lovastatin solution at a dose of 0.4 mg/kg was intraperitoneally administered to the crossed mice 6 times per week from day 3 after birth until day 28, and the mice were euthanized on day 29 for examination of the bodies and the bone formation in the same manner as above.

Figure 12A:
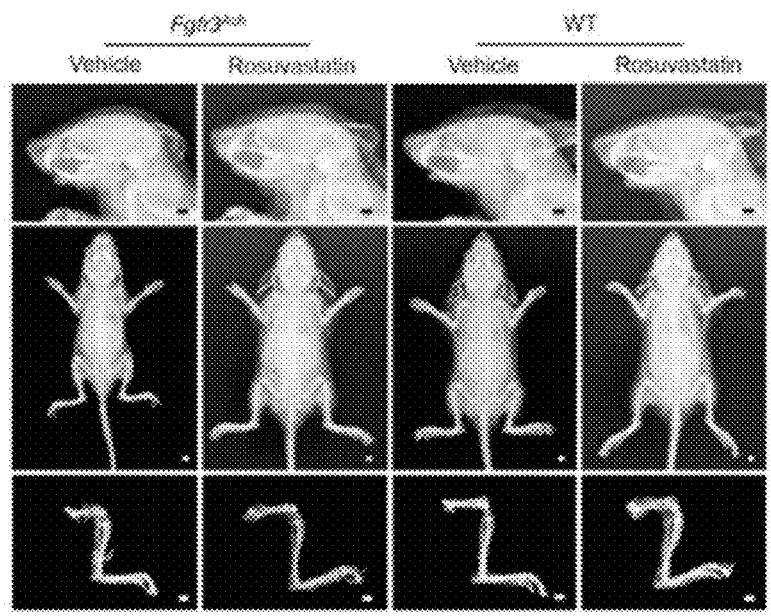
FIGS. 12A and 12B show the results of analysis of the bone growth of ACH model mice ($FGFR3^{Ach}$) treated with rosuvastatin.
Figure 12B:
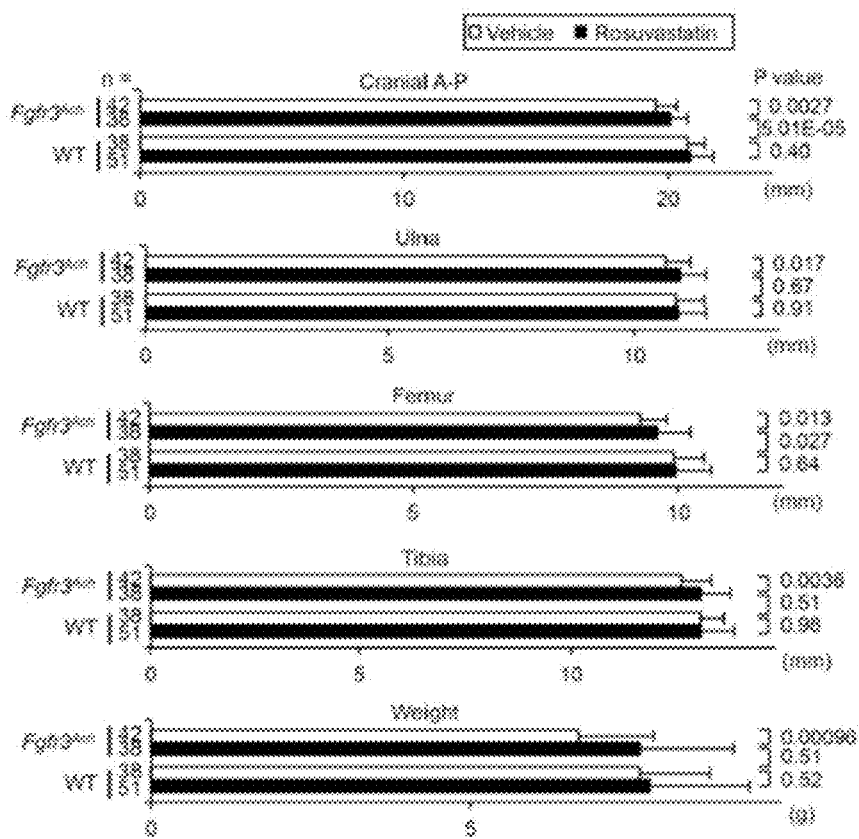
Figure 13:
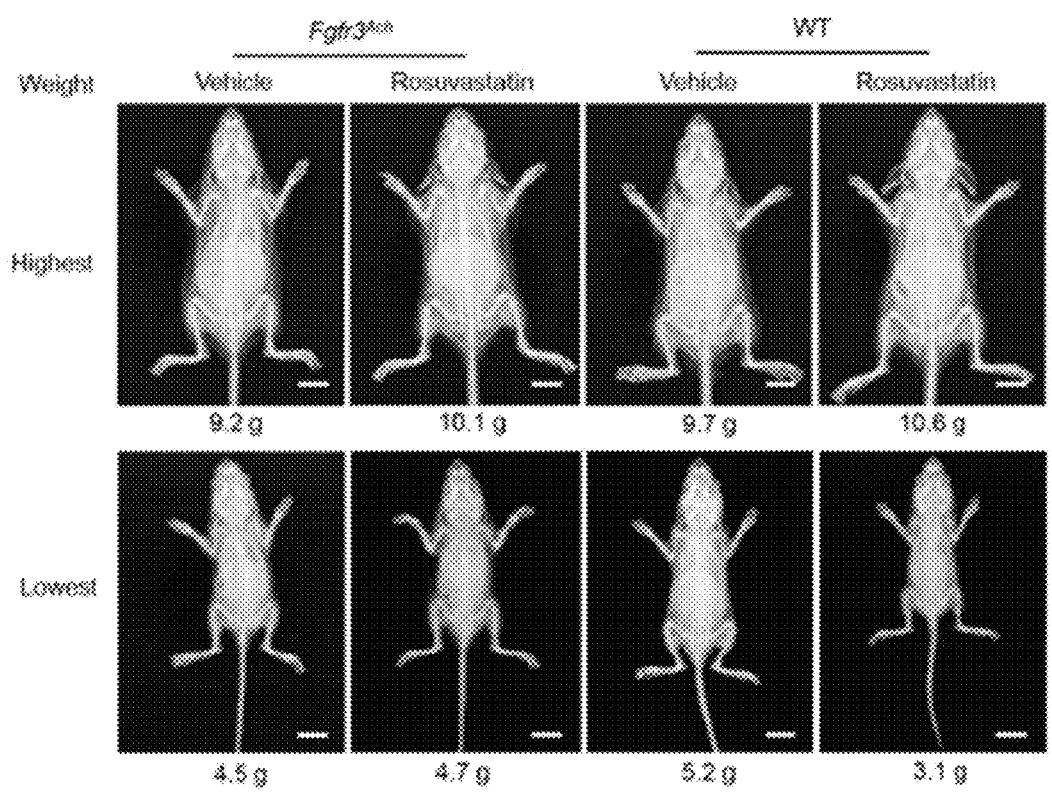
FIG. 13 shows the results of analysis of the size of the bodies of ACH model mice ($FGFR3^{Ach}$) treated with rosuvastatin. The X-ray images of the mice with the highest weights (Highest) and the lowest weights (Lowest) in each group are shown. The weight of each mouse is indicated at the bottom of each panel. The scale bar is 10 mm.

The FGFR3$^{Ach}$ mice show dwarfism, short limb bones and a short nose. Intraperitoneal administrations of rosuvastatin increased the anteroposterior lengths of the skulls (Cranial A-P) and the lengths of the ulnas (Ulna), femurs (Femur) and tibiae (Tibia) in the FGFR3$^{Ach}$ mice when they were 15 days old (FIGS. 12A, 12B and 13). There were no significant differences in the lengths between FGFR3$^{Ach}$ mice receiving rosuvastatin and wild-type mice receiving vehicle, indicating that rosuvastatin administration restores reduced bone growth to the nearly same shape as that of wild-type mice.

Figure 14A:
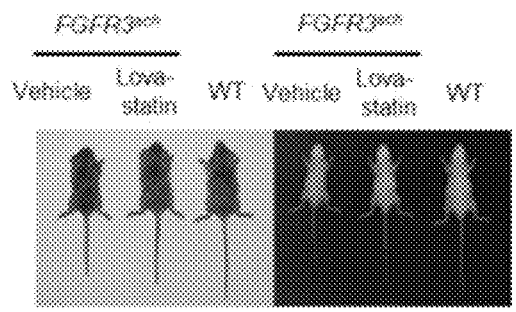
FIGS. 14A to 14D show the results of analysis of the bone growth of ACH model mice treated with lovastatin. Lovastatin was intraperitoneally administered to $FGFR3^{Ach}$ mice from day 3 after birth until day 28, and the analysis was performed on day 29.
Figure 14B:
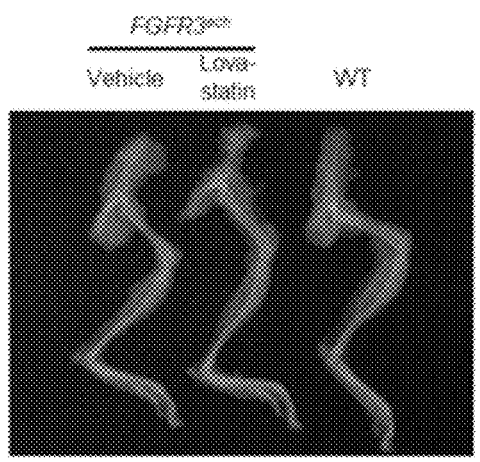
Figure 14C:
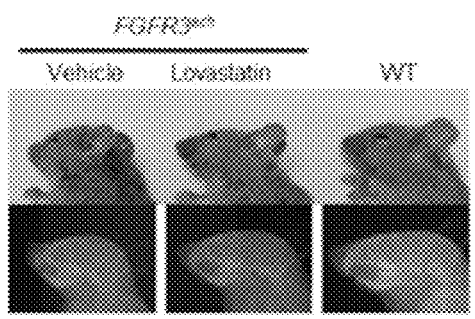
Figure 14D:
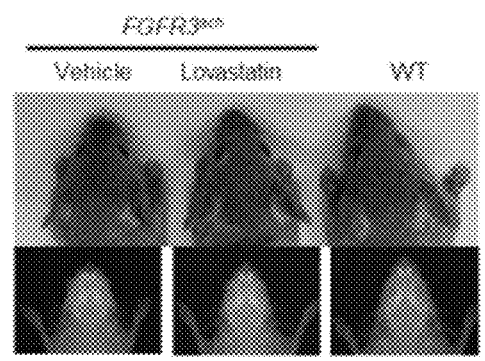
Figure 15:
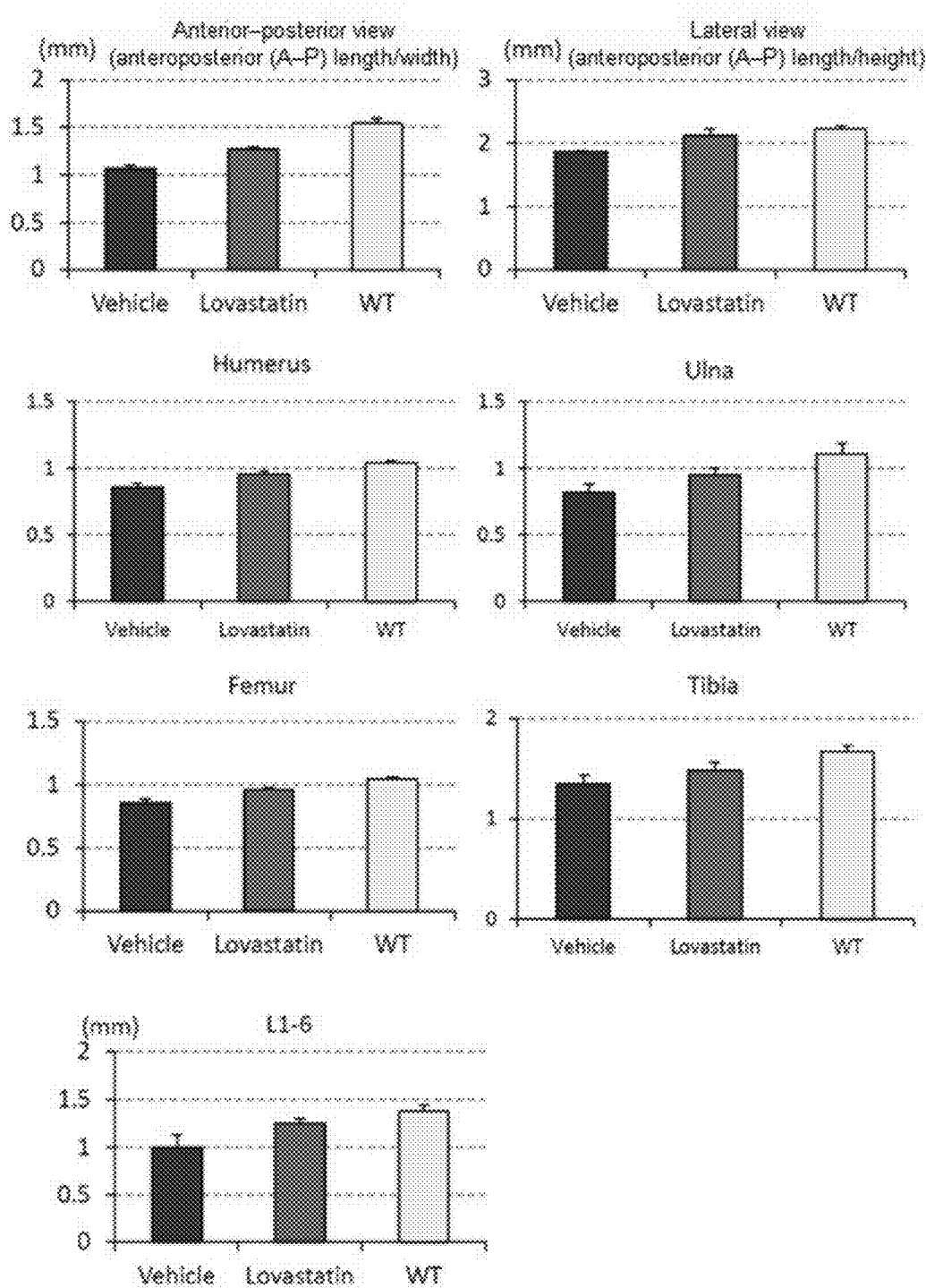
FIG. 15 shows the results of measurements of the length of various bones in $FGFR3^{Ach}$ mice treated with lovastatin.

Similarly, lovastatin administrations increased the lengths of the bodies and the long bones of the FGFR3$^{Ach}$ mice (FIGS. 14A, 14B and 15 and Table 5). Lovastatin administrations rescued the short nose of the FGFR3$^{Ach}$ mice to some extent (FIGS. 14C, 14D and 15 and Table 5). These results indicate statin administration also alleviates bone formation defects in the FGFR3$^{Ach}$ model mice.

TABLE 5

| | FGFR3 | | |
|---|---|---|---|
| | Vehicle | Lovastatin | WT |
| Anterior-posterior view (anteroposterior (A-P) length/width) | 1.07 ± 0.03 | 1.27 ± 0.025 | 1.54 ± 0.052 |
| Lateral view (anteroposterior (A-P) length/height) | 1.87 ± 0.0028 | 2.11 ± 0.12 | 2.23 ± 0.036 |
| L1-6 | 1.0 ± 0.13 | 1.25 ± 0.05 | 1.38 ± 0.057 |
| Humerus | 0.75 ± 0.05 | 0.88 ± 0.028 | 1.01 ± 0.028 |
| Ulna | 0.82 ± 0.057 | 0.95 ± 0.05 | 1.11 ± 0.076 |
| Femur | 0.86 ± 0.03 | 0.96 ± 0.02 | 1.041 ± 0.02 |
| Tibia | 1.35 ± 0.086 | 1.48 ± 0.09 | 1.67 ± 0.057 |

(Unit: mm)

Figure 16A:
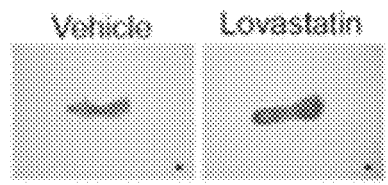
FIGS. 16A to 16G show the results of culture of chondrocytes with addition of lovastatin.
Figure 16B:
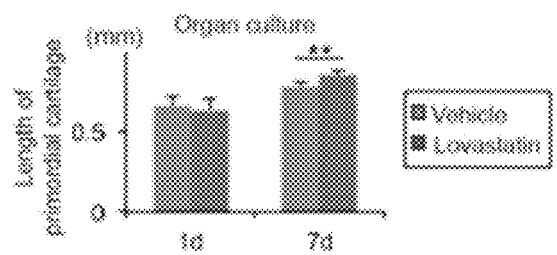
Figure 16C:
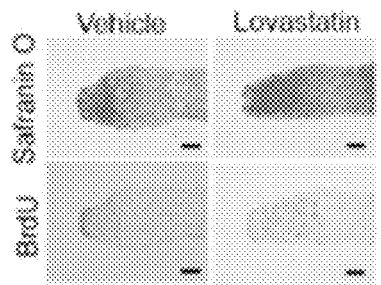
Figure 16D:
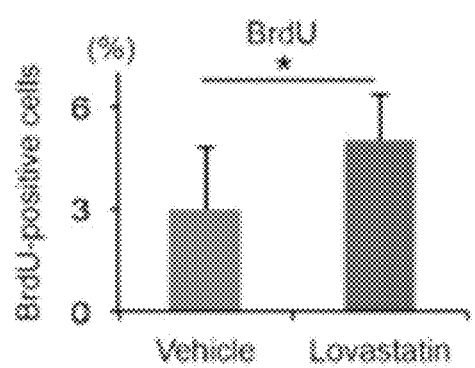

The lengths of primordial cartilage in FGFR3$^{Ach}$ model mice increased more in organ culture in the presence of lovastatin than in the absence of lovastatin (FIGS. 16A and 16B), indicating that lovastatin acts on the cartilage directly to induce its elongation. Incorporation of BrdU in the primordial cartilage revealed that lovastatin increased the proliferation capacity of the primordial cartilage in the FGFR3$^{Ach}$ model mice (FIGS. 16C and 16D). The organ culture was performed by culturing the metatarsal primordial cartilage of the FGFR3$^{Ach}$ model mice in the presence of lovastatin for seven days. Metatarsals were collected from 15.5 d.p.c. mouse embryos with a mixed FVB×C57Bl/6 genetic background, and were subjected to organ culture as described in Ikegami, D. et al., Osteoarthritis Cartilage 19, 233-241, 2011. Briefly, after the genotypes of the pups were determined, the metatarsals from FGFR3$^{Ach}$ mouse embryos were treated with 1 µM lovastatin or vehicle.

Figure 16E:
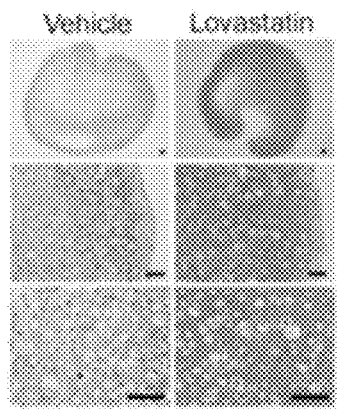
Figure 16F:
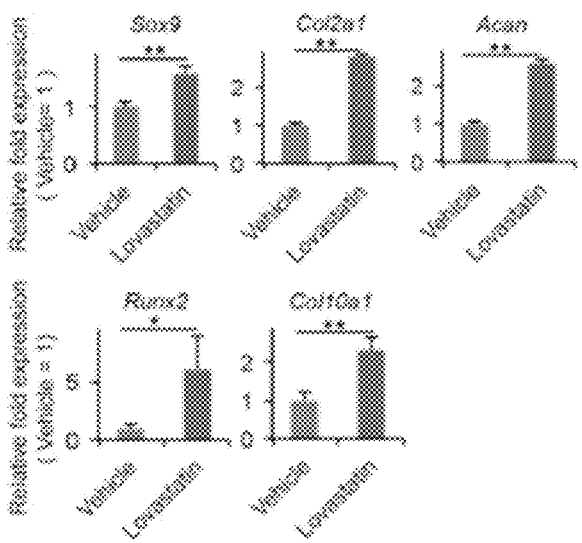

The pellets of FGFR3$^{Ach}$ mouse-derived primary chondrocytes cultured in the presence of lovastatin showed more intense safranin O staining than did the pellets of FGFR3$^{Ach}$ primary chondrocytes in the absence of lovastatin (FIG. 16E). FGFR3$^{Ach}$ pellets cultured in the presence of lovastatin showed increased expression levels of Sox9, Col2a1 and Acan at 2 weeks after the start of pellet culture, as well as increased expression levels of Runx2 and Col10a1 at 4 weeks after the start of pellet culture (FIG. 16F). Pellet culture was performed as follows. The primary chondrocytes used for culture were obtained from FGFR3$^{Ach}$ mice in accordance with the method described in Gosset, M et al., Nature protocols 3, 1253-1260, 2008. A total of 5×10$^5$ primary chondrocytes were transferred into a 15-ml tube and centrifuged at 200 g for 10 minutes. The resulting pellet was incubated for 2 or 4 weeks in the presence or absence of 1 µM lovastatin. The results suggest that addition of a statin stimulated both chondrogenic differentiation and maturation towards hypertrophy by increasing the expression of Sox9 and Runx2, respectively.

Figure 16G:
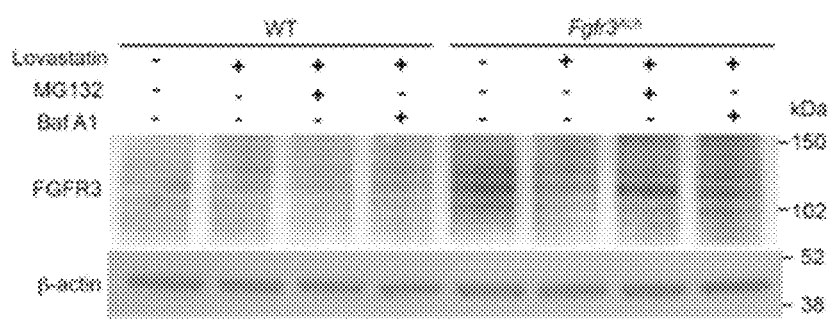

Expression level analysis of FGFR3 in the primary chondrocytes showed that a larger amount of FGFR3 was detected in the FGFR3$^{Ach}$ mouse chondrocytes than in the wild-type mouse chondrocytes (FIG. 16G). Addition of lovastatin to the culture decreased the amount of FGFR3 in the FGFR3$^{Ach}$ mouse-derived chondrocytes, and addition of the proteasome inhibitor, MG132 (Sigma), increased the amount of FGFR3 in FGFR3$^{Ach}$ chondrocytes that were cultured in the presence of lovastatin. The expression of FGFR3 was slightly increased in FGFR3$^{Ach}$ chondrocytes by the addition of the lysosome inhibitor, Bafilomycin A1 (Baf A1) (Sigma), in the presence of lovastatin in the cultures. The investigation of the effects of the inhibitors was performed as follows. A total of 2.5×10$^5$ primary chondrocytes were plated in each well of a six-well plate, and were cultured in the presence or absence of 1 μM lovastatin for 2 days. Then, the culture was supplemented with 10 mM MG132, 100 nM Baf A1 or vehicle. Two hours later, the culture was further supplemented with 50 ng/ml FGF9 (PeproTech) and incubated at 4° C. for 2 hours. Then cells were collected and subjected to analysis by Western blotting. The results suggest that statin treatment induced the degradation of FGFR3, through a proteasomal pathway.

INDUSTRIAL APPLICABILITY

The present invention is based on the success in reproduction of the clinical conditions of FGFR3 diseases by inducing the chondrogenic differentiation of iPS cells derived from the somatic cells of FGFR3 disease patients. The thus produced chondrocytes can be used to screen for a therapeutic and/or prophylactic agent for FGFR3 diseases. The present invention also provides a chondrogenic differentiation-promoting substance identified by the screening, and the substance can be used as a novel therapeutic and/or prophylactic agent for FGFR3 diseases.

The invention claimed is:

1. A method for treating a skeletal dysplasia involving abnormal bone formation due to FGFR3 mutations, the method comprising administering an effective amount of a statin to a subject in need thereof.

2. The method of claim 1, wherein the statin is a drug selected from the group consisting of mevastatin, atorvastatin, pravastatin, rosuvastatin, fluvastatin, pitavastatin, and lovastatin.

3. The method of claim 1, wherein the skeletal dysplasia involving abnormal bone formation due to FGFR3 mutations is thanatophoric dysplasia (TD) and/or achondroplasia (ACH).

4. The method of claim 1, wherein the statin is a drug selected from the group consisting of mevastatin, atorvastatin, pravastatin, rosuvastatin, fluvastatin and lovastatin.

* * * * *